（12） United States Patent
Noll et al.

(10) Patent No.: US 8,778,330 B2
(45) Date of Patent: *Jul. 15, 2014

(54) EN VIVO GENERATED TISSUE SYSTEM

(71) Applicants: Lee Noll, Whitmore Lake, MI (US);
Brian Hampson, Canton, MI (US);
Kristin Goltry, Milan, MI (US);
Samantha Snabes, Houston, TX (US)

(72) Inventors: Lee Noll, Whitmore Lake, MI (US);
Brian Hampson, Canton, MI (US);
Kristin Goltry, Milan, MI (US);
Samantha Snabes, Houston, TX (US)

(73) Assignee: Aastrom Biosciences, Inc., Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/793,332

(22) Filed: Mar. 11, 2013

(65) Prior Publication Data

US 2013/0295057 A1 Nov. 7, 2013

Related U.S. Application Data

(62) Division of application No. 12/615,446, filed on Nov. 10, 2009, now Pat. No. 8,394,632, which is a division of application No. 11/393,908, filed on Mar. 31, 2006, now Pat. No. 7,682,822.

(51) Int. Cl.
*C12N 5/074* (2010.01)

(52) U.S. Cl.
USPC ....... 424/93.21; 424/93.7; 435/399; 435/401; 435/347; 435/377

(58) Field of Classification Search
None
See application file for complete search history.

(56) References Cited

U.S. PATENT DOCUMENTS

| 5,716,616 | A | 2/1998 | Prockop et al. |
| 5,763,279 | A | 6/1998 | Schwarz et al. |
| 5,786,215 | A | 7/1998 | Brown et al. |
| 6,048,721 | A | 4/2000 | Armstrong et al. |
| 6,228,607 | B1 | 5/2001 | Kersten et al. |
| 6,642,019 | B1 | 11/2003 | Anderson et al. |
| 6,875,605 | B1 | 4/2005 | Ma |
| 6,943,008 | B1 | 9/2005 | Ma |
| 8,394,632 | B2 * | 3/2013 | Noll et al. ..................... 435/401 |

FOREIGN PATENT DOCUMENTS

| EP | 0 334 506 | 9/1989 |
| WO | WO 2004/039939 | 5/2004 |
| WO | WO 2005/007799 | 1/2005 |

OTHER PUBLICATIONS

Blood, Larry C. Lasky, et al., Nov. 16, 2004, vol. 104, No. 11 (Part 2 of 2 Parts), "Development of a 3D Perfusion Bioreactor System for Continuous Production of Hematopoietic and Blood Cells."
FASEB meeting Abstract, Mar. 31, 2005 to Apr. 14, 2005, Microenvironment of a Hematopoietic 3-D Culture.
American Society of Cell Biology Meeting Abstract, "Hematopoietic Stem Cell Localization on a 3-D Matrix", Dec. 10-14, 2005.
The International Search Report of the International Searching Authority for PCT/US2007/062166, date completed Jun. 28, 2008, date mailed Jul. 14, 2008.

* cited by examiner

*Primary Examiner* — Jim Ketter
(74) *Attorney, Agent, or Firm* — Miller, Canfield, Paddock and Stone; John H. Engelmann

(57) ABSTRACT

The present invention relates to methods of generating an ex vivo tissue-like system in a bioreactor system capable of supporting continuous production of, and output of cells and tissues and an ex vivo tissue system made therefrom.

2 Claims, 13 Drawing Sheets

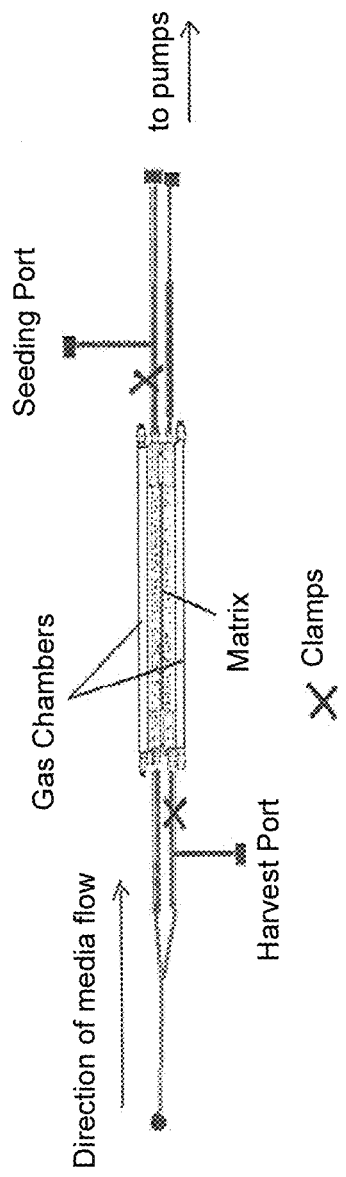

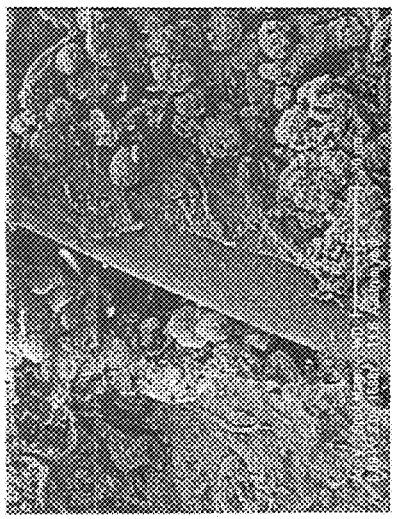
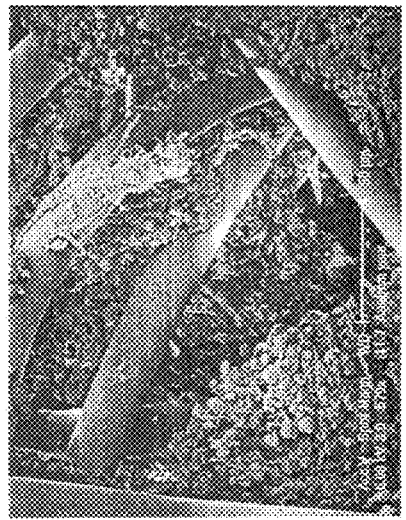
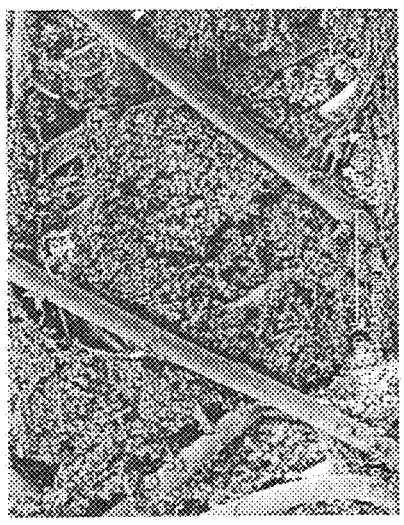
Figure 6-continued

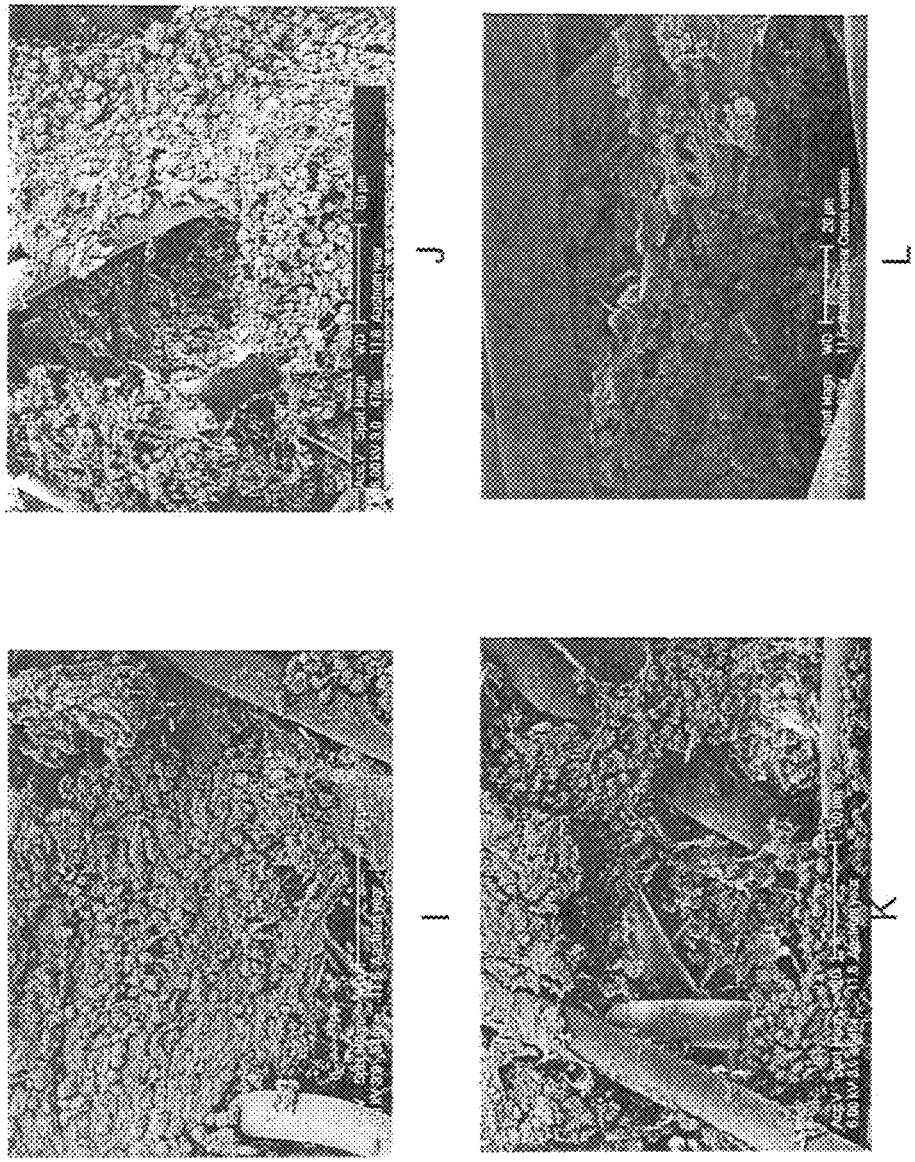
Figure 6-continued

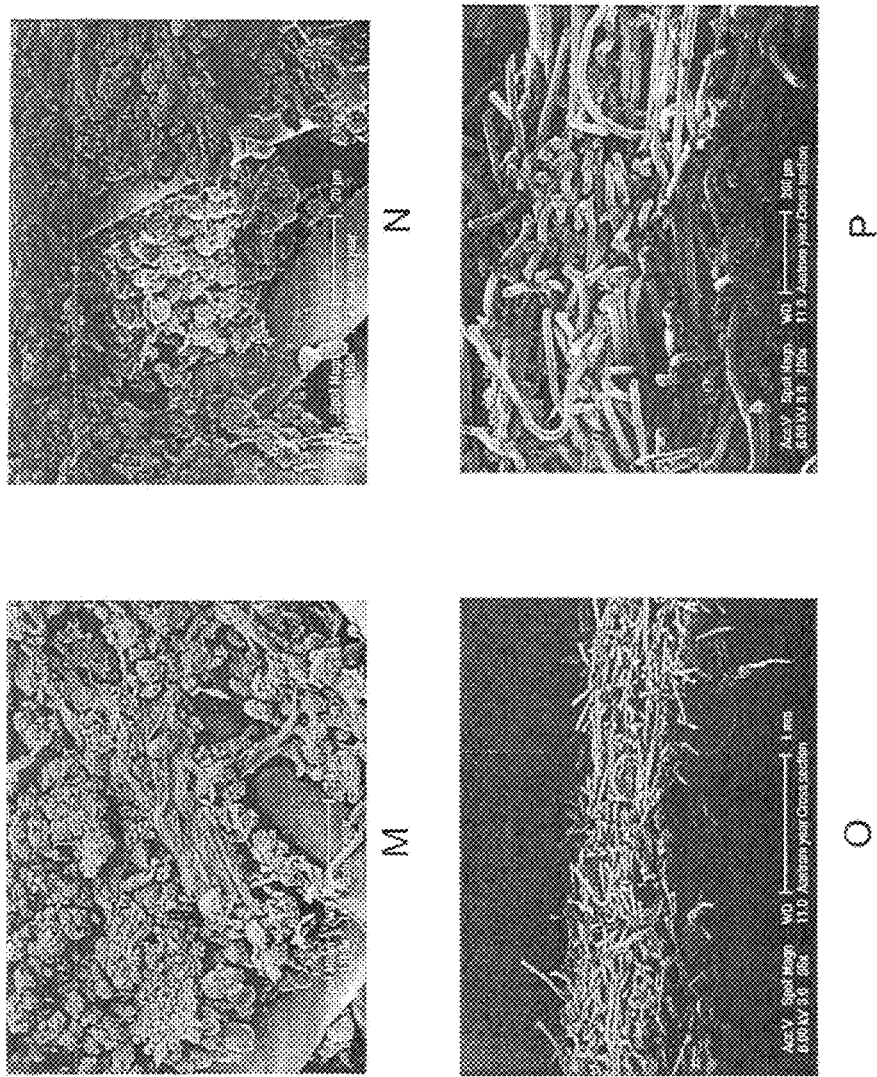

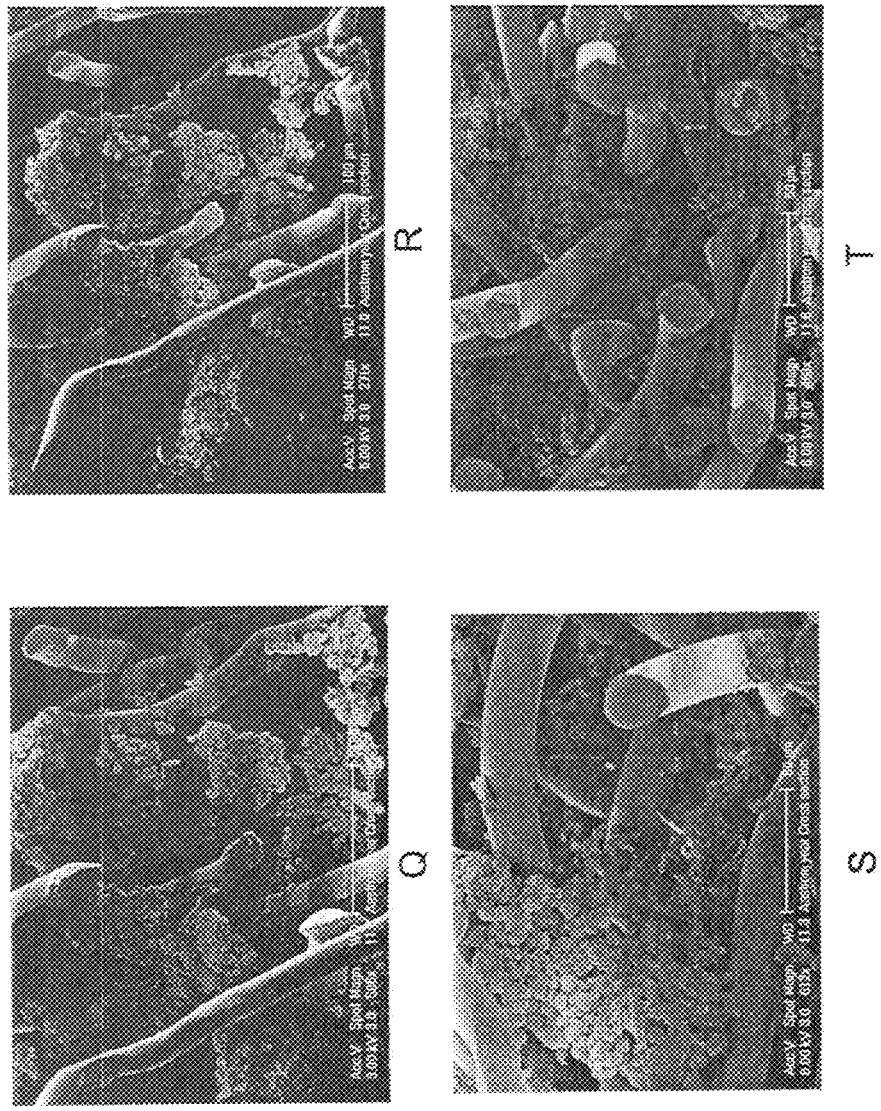
Figure 6-continued

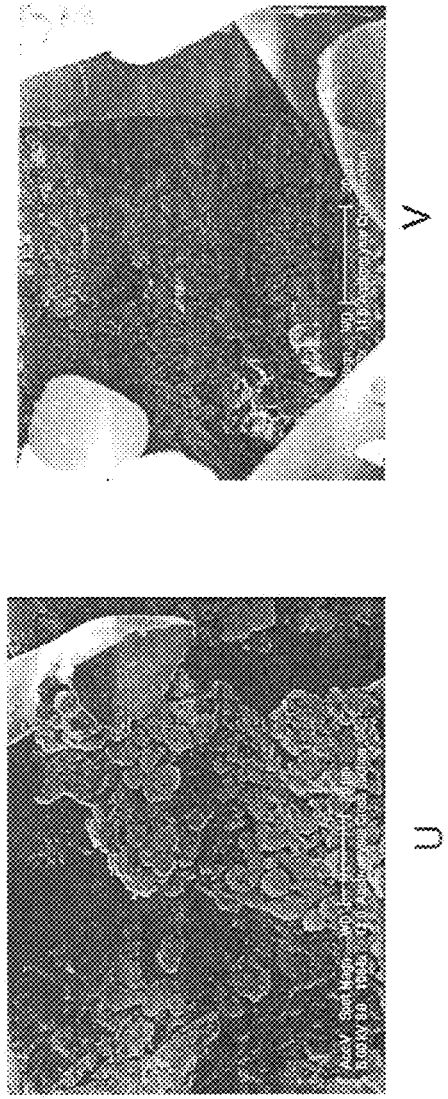

US 8,778,330 B2

EN VIVO GENERATED TISSUE SYSTEM

This application is a divisional application of U.S. application Ser. No. 12/615,446, filed on Nov. 10, 2009, which claims priority to U.S. application Ser. No. 11/393,908, filed on Mar. 11, 2006. The contents of the aforementioned applications are incorporated herein by reference in their entirety.

STATEMENT REGARDING FEDERALLY SPONSORED RESEARCH

The United States Government has rights in this invention pursuant to DARPA grant DAMD17-02-1-0704.

BACKGROUND OF THE INVENTION

1. Field of the Invention

The present invention relates to methods of generating an ex vivo tissue-like arrangement in a bioreactor system capable of supporting continuous production of, and output of cells and tissue and an ex vivo tissue system tissue made therefrom.

2. Discussion of the Background

There is significant interest using both early and lineage committed cells and organized tissues for a variety of therapeutic and research purposes.

In tissue engineering, the goal is to reconstitute fully or partially functioning human tissue in vitro to enable a variety of clinical, investigational and other applications. Several studies have been carried out that are aimed at reconstituting functioning human tissues in vitro.

The hematopoietic system exemplifies the broad range of cells involved in protection of mammalian hosts against pathogens, toxins, neoplastic cells, and other diseases. The hematopoietic system is believed to evolve from a single stem cell, from which all the lineages of the hematopoietic system derive. Hematopoietic cells have been used in human therapy. Methods and apparatuses for culturing precursor hematopoietic cells to obtain desired mature hematopoietic cells have beers described. See, U.S. Pat. Nos. 5,605,822, 5,399,493; 5,437,994; 5,459,069; 5,635,386, 5,670,147 and 5,670,351.

In addition, bioreactor systems have been described in U.S. Pat. No. 6,875,605 and U.S. Pat. No. 6,493,008, these bioreactor systems, however yield poor cell numbers in long-term culturing and fail to generate tissue-like matrices within the bioreactor because the master in which the media was provided did not allow entrapment of non-adherent cells.

A bioreactor system has also been described and presented at the American Society of Hematology held in San Diego Calif. on Dec. 4,-7, 2004 (Abstract published in *Blood*, vol. 104(11):Nov. 16, 2004). This bioreactor system was composed of a polycarbonate bioreactor body using a nonwoven polyethylene terephthalate matrix in which cord blood derived stem cells or HS-5 cells were cultivated using recirculating or single pass culturing techniques also using an external gas exchanger. The matrix material used as a scaffold for the cultured cells appeared to have limited biocompatibility. The combination of matrix material, method of cell seeding and the way the reactors were incorporated into a nutrient delivery system combined to make the system sub-optimal. Toxicity issues were still apparent in these designs.

These prior devices are unable to support tissue-like culture density due to a poor gas exchange mediated by the gassing membrane, which prevents migration of the cells into the depth of the support matrix, which, in turn, does not permit the establishment of a gradient of media and growth factor availability to the cells mimicking intact human tissues.

Still further, as the gas exchange is so poor in these prior devices, increased gas delivery is to be provided by increasing the flow rate of the media with gas being provided though as external source.

Moreover, these prior devices do not generate ex vivo tissue because, the fluid pathway is too thick and requires seeding through a depth filter method, resulting in the removal of non-adherent cells, which significantly impairs the long term ability of the culture to generate a tissue and maintain function. Overall, the general goal of the above methods and other prior methods and devices was to optimize culturing conditions for homogenous cultures of specific cell types (whether mixed with additional support cells or contaminants.)

There remains a need for apparatus that maintains a culture of either homologous or heterogonous cells in an organized arrangement in three-dimensions and allows the development of differing microenvironments conducive to tissue expansion and maintenance for extended periods of time with the ability to change the microenvironment parameters within the culture and which can permit the ex vivo generation of tissue-like matrices of cells.

SUMMARY OF THE INVENTION

Accordingly, it is an object of this invention to provide an apparatus in which a mixed population of cells such that the cells are provided with the environment where they can reorganize into a tissue-like array and which can be maintained without sub-culture for extended periods of time, and have the capacity to support tissue function.

It is another object of the invention to provide a flexible apparatus that allows mechanical manipulation of the way that the culture is managed that either directly or indirectly affects the interactions of the microenvironment to induce and maintain varying tissue structures.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 3 schematically depicts the cross-flow generation of fluid shear in the 3-D bioreactor design FIGS. 4 A-C depict graphs of cell counts where (A) is sloughed cell harvest output, (B) is Total Sloughed Cell yield in each harvest, and (C) is combined daily sloughed cell harvest.

DETAILED DESCRIPTION OF THE INVENTION

Figure 1:
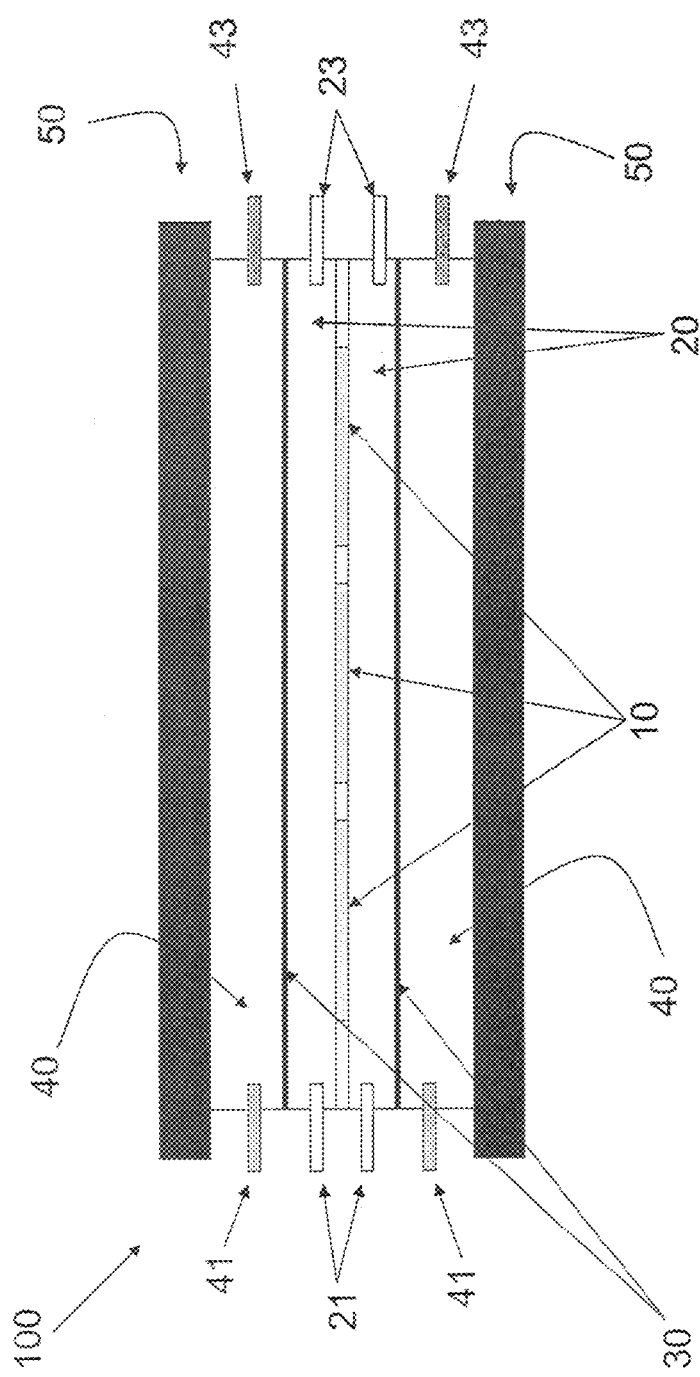
FIG. 1 is a schematic view of a bioreactor described herein.

Most tissues and organs consist of multiple cell types organized into a synergistic relationship with other cells, cell types sad support structures. Combinations of both contact and non-contact signals are necessary for proper function.

The bioreactor described herein, with its matrix substrate, allows the cells with a common structure and function to organize into areas where the local milieu or microenvironment is similar to their tissue origin, e.g., hypoxic or oxygenated, low or high nutrient levels, low or high pH levels and others. These tissues are normally held together by an extracellular matrix that provides a web upon which the cells attach and allows them to weave together into a structured organization. The matrix of the bioreactor forms the support that allows the cells to first attach, migrate to areas within the tissue most conducive to their growth, and start producing their own extracellular matrix. These cells can then arrange naturally to form tissue. Cells within the tissue that have the highest metabolic requirements form along the surfaces of the matrix and into the larger open areas where there is little diffusive resistance to nutrient and gas availability. Under this layer, deeper within the matrix and within the tighter openings, cells that have a lower metabolic requirement will tend to migrate and form in their more optimal microniche.

The system described herein provides a uniquely flexible system enabling long-term culturing of cells and tissue-like matrices as well as the generation of the same. This system in terms of both physical and chemical characteristics, for example, of the three-dimensional matrix material used in the system can be changed easily to meet the demands of culturing certain types of cells and/or for generating different types of tissue-like structures. In addition to the physical characteristics of the matrix itself, the system and devices described herein enable one to manage the culture to direct and control the fate of the cultured cells and/or tissue. This system and device permit the ability to closely mimic and control biologically important gradients (nutrient, physiological gasses, metabolic by-products, control and signaling factors, etc.), flow dynamics, shear, fluid to cell number ratio, single pass and/or recirculated media management continuous, semi-batch or batch media exchange controlled and localized delivery of growth factors, and others required to mimic the targeted in vivo tissue.

As used herein "ex vivo generated tissue" or "tissue-like matrix" means a culture of cells contained in a three-dimensional scaffold or matrix of the bioreactor as described herein that has a mixed population of cells that mimics at least one biological indicia of naturally occurring tissue found in a human or mammalian body. Non-limiting examples of such tissues include liver, kidney, gastrointestinal, respiratory, cartilage, thymic, lymphatic, pancreatic, bone, bone marrow, blood, epithelial, cardiac, adipose, and skin.

The bioreactor for the ex vivo generation of tissue-like matrix offers a unique and flexible perfusion or flow-through system capable of supporting continuous production and output of a variety of cell products, cells and tissue types over extended periods of time, e.g., months. The bioreactor can be composed of: 1. a cell attachment/immobilization surface or 3-D cell matrix, 2. a fluid space or spaces bathing the cell scaffold from above and below defined by the bioreactor body providing the depth of the fluid layer through which the metabolic gasses must diffuse, 3. gassing membrane (s) defining the edge of the fluid space above and/or below the cell scaffold, and 4. membrane restraint(s) to keep the flexible gas membrane from bowing or bulging away from the cell scaffold. Additionally, one or two gas chambers may be defined above (and below) the membrane restraint allowing the mixed metabolic gasses to be confined to the area above the top, and or below the bottom gassing membrane.

In one embodiment, the bioreactor is designed such that flow through the bioreactor may be along and/or through the cell bed or cell space, allowing replenishment of nutrients and gas exchange without exposing the cells in she cell-matrix construct to high flow rates, or may be modulated with a portion of the flow being directed through the cell space to modify and control the diffusion gradients within the tissue construct. The system is flexible; as it can accommodate a broad repertoire of cell-matrix constructs to include multiple form factors and configurations, ranging from fibers to hydrogels. The bioreactor allows a variety of approaches to maintenance of cell-matrix constructs (e.g., single pass or recirculation) and collection of cells and cell-matrix constructs.

The bioreactor has dual oxygenation capabilities, with a gas-permeable membrane overlying the cell-matrix constructs, and an optional hollow-fiber oxygenator in series with the bioreactor. In one embodiment, the bioreactor is configured with integrated gassing membranes allowing the decoupling of metabolic gas supply and control from the delivery of liquid nutrient solutions. A harvest port can be provided in line with the bottom of the bioreactor for in-line harvest of cell that slough from the matrix and settle downward. The bioreactor may be inclined such that sloughed cells are either continually removed from the reactors by the nutrient flow (down-ward flow), or inclined such that the released cells are retained within the reactor until manually harvested (upward flow). The bioreactor can be composed of modules that can be arranged in series and in parallel.

A supporting apparatus can be used to integrate the bioreactors to provide recirculation, removal of waste and/or delivery of fresh medium, for example, such supporting apparatus can mimic the recirculation system of the human, mammalian or other animal body. In some embodiments, the bioreactor can be connected to a reservoir such that fresh media or recycled media can be equilibrated in the reservoir before being provided to the cells in the bioreactor.

This bioreactor system can also be useful for the study and production of products in a true tissue organization in three dimensions. Standard cell culture has been traditionally conducted on planar surfaces where the ability to visualize the progress of the culture is an important factor or in suspension culture. Animal and plant cells rarely exist as singular cell types in single level planar arrangements, or floating in fluids (except in peripheral blood). Most require 3-D scaffolding and organization of multiple cell types to exhibit full functional characteristics that are evident in their natural tissue arrangement in vivo. Standard cell culture devices have been designed to provide a homogeneous environment to simplify the study of these cultures and control methods. This approach rapidly encourages only the cells that do well in this homogeneous environment to rapidly "smother out" the cells that do not prefer this supplied homogeneous condition.

The bioreactor can be used to mimic the natural microenvironment for tissue where non-homogeneity is the rule. These cells require natural gradients of nutrient and metabolic gas availability, concentration gradients of metabolic waste and by-product, and stimulatory/growth and regulatory factors. Under these natural-like conditions, the individual cells and multiple types that comprise a tissue, function in a biologically competent way can be obtained. The bioreactor can also be used to maintain and expand the culture of cells and tissues for extended periods of time, e.g., more than one year, without subculture.

The bioreactor can be used as a source of cells or cell-matrix constructs/tissues for marrow replenishment and plastic transformation into other tissues and organs, leading to new approaches for treating a variety of disorders and/or conditions in a patient, e.g. irradiation and traumatic injuries, among others. Observation of lymphohematopoiesis in the system can lead to gains in knowledge of immune function in general, applicable to a large variety of disorders.

The bioreactor's ability to culture cells for extended periods of time can be used to obtain new insight by observing sustained hematopoiesis for those extended periods of time, e.g., up to or more then one year. The bioreactor may be used as part of (and to house) an entire artificial immune system that can be used for rapid vaccine testing and for evaluation of the immune response to any antigen or foreign material/chemical. The developed system, and the cells it produces, may provide an alternative to use of embryonic stem cells. Alternatively, the system may be used so expand embryonic stem cells for lymphohematopoietic and other cell and tissue use. The longevity of the culture may allow for now or easier tissue expansions that short term cultures do not permit.

Referring now to the drawings, wherein like reference numerals designate identical or corresponding parts throughout the several views.

FIG. 1 is a schematic view of the bioreactor according to the present invention. As shown in the figure, in a preferred embodiment the bioreactor 100 includes, among other components, a scaffold or matrix 10, two fluid chambers 20, two membrane members 30, and two gassing chambers 40. These and other components of the bioreactor 100 are described below.

The scaffold 10 can be used to immobilize cells, such as by attachment of the cells or by entrapment of the cells. In one embodiment, the cell support scaffold 10 (either singular or multiple) is affixed into the bioreactor body.

The scaffold or matrix member 10 can permit attachment of the cells thereto or can entrap the cells therein. The matrix member 10 can be a two dimensional-or three dimensional matrixes, and can be manufactured from a material that does not adversely affect cell growth, reproduction, or population. In a preferred embodiment, the matrix is three dimensional. Examples of suitable materials include plastic, glass, ceramic or natural biomatrix materials such as collagen, alginates, proteoglycans and laminin. When the matrix member 10 is a three dimensional matrix, the matrix member 10 cats include either geometrically or randomly arranged portions, such as holes or pores, which immobilize the cells. The three dimensional matrix member 10 can be manufactured from one or both of non-woven and woven fibers, having an ordered or random fiber arrangement. An example of a suitable non-woven fabric having a random fiber arrangement is polyester material such as a felt fabric formed from polyethylene terephthalate (PET). Preferably, the matrix ember 10 is a three dimensional matrix manufactured from a polyester fiber, which has a random fiber arrangement. In preferred embodiments, the three dimensional matrix can be composed of biocompatible material or a mixture of materials organized in a manner that optimizes cellular communication in the formation of the desired tissue. For example, the matrix can be arranged in a variable relationship between tight and broad spacing between the pores of the matrix member. In a preferred embodiment, the matrix material is biocompatible and devoid of toxic chemicals such as silver ions. The investors have found that inclusion of such silver ions is the matrix material significantly impairs the culturing of cells.

Different matrix materials can be placed in the bioreactor to match the spatial configuration and chemical make-up as required by different tissues, changes in the way that both nutrients and metabolic gasses are delivered to allow the development of micro niches that most closely match the natural microenvironment for the tissue.

Surgical implant fabrics are available in a wide range of fabric types from the very loose non-woven felt-like materials to the more closely oriented fibers of the spun yarn that is woven into either knits or velour fabrics. The tightness of the yarn, the weave pattern, and tightness of the weave all combine to control the fiber-to-fiber spacing, i.e., porosity seen by cells in the culture. Additionally, these fabrics can be processed to control their wettability and protein binding capacity. Specific attachments proteins can also be provided to the fibers of the fabric to enhance the attachment of specific cells and growth factors to enhance tissue development.

The choice of matrix can be used to establish the base-line of the types of cell that will be released from the culture and also the type of ex vivo tissue generated therein. As discussed further below, the combination of the type of matrix coupled with manipulations of nutrients, fluid flow rate, parallel or cross-flow, media exchange rate and gas mixture provide a powerful system to manipulate a culture of cells to arrange in near-tissue like structures.

The scaffold or matrix member 10 can be varying dimensions to accommodate far a number of various ex vivo tissue generation protocols. In certain embodiments, the scaffold or matrix member can be from about 0.5 to about 3 mm thick. However, one will appreciate that this thickness can be varied depending on the combined density of both the scaffold and/or matrix material and the density of the cells and/or tissue(s) associated with the scaffold/matrix to accommodate accessibility of the metabolites and other nutrients, growth factors etc. provided to the cells and/or tissue(s). In some embodiments, 1 mm thick matrices that have as small as 2 to 5 cell diameters and up to 300 micron pores can be used.

The matrix member 10 can be disposed in a void formed in the bioreactor or a support, such as a through hole between top and bottom surfaces of a support member. In a preferred embodiment the matrix member 10 is removably retained in such a through hole, so that removal and, in some embodiments when one is to reuse the bioreactor, replacement of the matrix member 10 from the support can be easily accomplished by removal and replacement of a snap ring. The matrix member 10 can also be removably retained in the support member by one or more other components. It is to be understood, however, that the matrix member 10 can alternatively be irremovable disposed in the support member to prevent removal of the matrix member 10 from the support.

In one embodiment the support member is removably disposed in the bioreactor 100, such that removal of the entire scaffold 10, including the matrix member 10 and the support member, can be accomplished as a single unit, sad such that the matrix member 10 and the support member can be replaced as a single unit. Alternatively, the support member can be irremovably disposed in the bioreactor 100.

Components of each of the matrix member 10 and the support member of the scaffold 10, as well as other components of the scaffold 10, can be manufactured from an inert material that does not adversely affect cell growth, reproduction or population. In one embodiment, the components can be made, independently of each other, any biocompatible solid, e.g., TEFLON® or polycarbonates, preferably the material is sterilizable through conventional methods known in the field.

The components of the scaffold 10 are manufactured from an inert plastic material. For long-term hematopoietic model of the bone marrow compartment, the matrix material can be made of a non-woven or woven fabric made from twisted fibers. Generally, the matrix material support cell growth, and maintenance should be stable and not degraded by the tissue over the period of time in which it is used in the bioreactor system. In certain embodiments, where the tissue-like matrix and/or cells attached to the matrix material are transplanted directly into the body, for example, cartilage, a fabric or matrix is preferably used that can be reabsorbed by the body after implantation.

Although the drawings show the preferred embodiment in which the scaffold 10 includes a single matrix member 10, it is to be understood that a plurality of matrix members 10 can be included. Further, a combination of two dimensional, and three dimensional matrix members 10 can be disposed on a single support member and can have the same and/or different porosities as compared to one another. It is also to be understood that although the drawings show the use of a single scaffold 10, the bioreactor can include a plurality of scaffolds 10, and that each of the scaffolds 10 can include one or more matrix members 10.

In certain embodiments, two or more matrices can be stacked together within within the bioreactor to facilitate the formation of ex vivo generated tissue-like matrices. In the these types of arrangements, the individual matrix layers/sections can be seeded individually, with similar inoculum materials, different cell types and either at the same time or separate times. Additionally, a single matrix of these arrangements and desired cells can migrate naturally to the appropriate matrix and microenvironment.

Multiple matrix members (same or different materials with the same or different compositions and/or geometries) may be serially disposed within a single bioreactor or may be stacked and loaded with different cell types that when layered, simulate the organization of a complex tissue, for example, a endothelial layer over a thymic equivalent which facilitates education of loaded dendritic cells prior to delivery of antigens to naive T-cells.

The fluid chamber 20 can provide at least one of a fluid containing cells and a cell nourishing medium to the matrix member 10, such that the cells are immobilized by the matrix member 10, and the cells is the matrix member 10 receive the nourishing medium. A fluid chamber 20 extends such that the fluid flows from a fluid chamber input 21 to a fluid chamber output 23, about perpendicular to a surface of the matrix 10 exposed to the fluid. In one embodiment, the fluid flows from the fluid chamber input to a fluid chamber output about parallel to the surface of the matrix 10 carrying cells exposed to the fluid. Thus, by this arrangement, all the fluid introduced into the fluid chamber 20 does not flow through the matrix member 10. It is to be understood, however, that the fluid chamber 20 is not required to extend about parallel to the matrix member 10, and can extend at any angle relative to this surface of the matrix member 10. Further, the fluid chamber 20 can extend such that all the fluid introduced in through the fluid chamber input 21 and flowing out through the fluid chamber output 23 flows through the matrix member 10. Preferably the chamber 20 has a depth that does not limit the growth of the cells in the matrix, such as a depth of from about 1 mm to about 10 mm.

In some embodiments, ports are integrated into one or more of the fluid chamber inputs or outputs to provide a way in which sells and/or media can be collected for analysis with disturbing the whole culture. Moreover, such ports can be used to deliver additional materials to the bioreactor simply and efficiently.

The flow of fluid can be managed to control the way that nutrients are delivered to the tissue. For example, when the flow of the fluid is entirely parallel to the matrix, the delivery can be by diffusion. A portion of the flow may be diverted through the matrix to reduce the diffusion gradient that is inherent in condition above. In another embodiment, the flow of the fluid is forced through the matrix carrying the cells/tissue whereby the diffusion gradient can be minimized; however such a flow of the fluid through the matrix can result in greater shear to the cells/tissue carried on the matrix.

Cells can be harvested as they naturally release from the matrix material and can be collected though the ports discussed above, a lower fluid chamber of the bioreactor, or another inlet or outlet as desired. In addition to or alternatively, the cells can be harvested by adjusting the flow of the media through the matrix to release cells from the matrix material. Adjusting the flow can be accomplished by redirecting the medium input and/or outputs such that the medium, for example, is forced to come in from the top of the bioreactor, flow through the matrix material, and flow out through the bottom of the bioreactor.

Preferably, the fluid chamber 20 is removably disposed in the bioreactor 100. Alternatively, the fluid chamber 20 can be irremovably disposed in the bioreactor 100. Components of the fluid chamber 20 can be manufactured from an inert material that does not adversely affect cell growth, reproduction or population. In the preferred embodiment the components of the fluid chamber 20 are manufactured from an inert plastic material. In one embodiment, the fluid chamber 20 is made from polytertrafluoroethylene or perfluoroalkoxy polymer resin.

In a preferred embodiment shown in the drawings the bioreactor 100 includes two fluid chambers 20 disposed on opposite sides of the scaffold 10, the two fluid chambers 20 extending in an about same direction parallel to one another and to the surface of the matrix member 10 which is exposed to the fluid. By this arrangement, the same or different fluids can be flowed on both sides of the matrix member 10. It is to be understood, however, that the bioreactor 100 can include one fluid chamber 20, or can include three or more fluid chambers 20. Further, the bioreactor 100 that includes three or more fluid chambers 20 can, but used not, include one of the scaffolds 10 disposed between each of the two adjacent fluid chambers 20. Further, when the bioreactor 100 includes the plurality of fluid chambers 20, the fluid chambers 20 can, but need not, extend in the same direction relative to each other or relative to the surface of the matrix member 10 which is exposed to the fluid.

The membrane member 30 preferably include a gassing membrane that is permeable to a gas, such as a metabolic gas, to be delivered to the fluid flowing in the fluid chamber 20 and ultimately to the cells immobilized in the scaffold 10. The gassing membrane can be used to close one side of the fluid chamber 20. By this arrangement, fluid introduced into the fluid chamber input 21 flows between the gassing membrane and the scaffold 10 before flowing out of the fluid chamber output 23. The metabolic gas can flow through the gassing membrane.

In a preferred embodiment the gassing membrane 30 is relatively impermeable to the fluid in the fluid chamber 20, such that the fluid in the fluid chamber 20 is not permitted to flow out of the fluid chamber 20 through the gassing membrane. Further, the gassing membrane can be of a thickness that does not inhibit the flow of the gas through the membrane. Although the gassing membrane can be manufactured from an inert material that does not adversely affect cell growth, reproduction or population, the material of the gassing member 31 preferably limits cell adhesion to the surface of the member. Preferably the gassing member 31 is relatively thin, such that the thickness of the gassing member 31 does not adversely limit the rate through which the gas can be delivered through the gassing member 31. In one embodiment, the gassing membrane can be 0.001 inches thick. The gassing membrane can be made from a number of gas permeable materials including TEFLON® (polytetrafluoroethyene-FEP) silicone materials, TPO, low density polyethylene (LDPE), ethylene vinyl acetate (EVA), and other polymeric materials that are both gas permeable and biocompatible (e.g., are not toxic to the cells being cultured). In one preferred embodiment, the gassing membrane is, in part or in its entirety, composed of FEP.

Although not required, the membrane member 30 can include a membrane restrain that restrains or limits the deflection of the gassing membrane. The membrane restraint can be in the form of an extended edge of the membrane member that limits deflection. It is to be understood that the membrane restraint can be in any form, however, so long as deflection of the gassing membrane is limited by the restraint and that the membrane member 30 need not include the membrane restraint. Preferably the membrane restraint does not cover so much of a surface of the gassing member such that the rate at which the gas can be delivered through the gassing member is adversely limited either in bulk or at a local scale, for example, holes can be both small and closely spaced such that diffusion "shadowing" does not occur.

Preferably, the membrane member 30 is removably disposed in the bioreactor 100, such that removal of the membrane member 30, including the gassing member and the optional membrane restraint, can be accomplished as a single unit, and such that the gassing member and the membrane restraint can be replaced as a single unit. Alternatively, the membrane member 30 can be irremovably disposed in the bioreactor 100.

Components of the membrane member 30, including the optional membrane restraint, can be manufactured from an inert material that does not adversely affect cell growth, reproduction or population. Preferably, the components of the membrane member 30 are manufactured from an inert plastic material. It is also preferred that the membrane restraint is manufactured from a transparent or translucent material, such that observation of the fluid movement below the gassing membrane is permitted. In one embodiment, the membrane member 30 and the membrane restraint. If included, can be composed of polytetrafluoroethylene. The membrane restraint can be in the form of a perforated plate sealed to the bioreactor body using an O-ring or other suitable configuration. Other materials can be used, such as fluoroelastomers (e.g., VITON® and copolymers of butadiene and acrylonitrile (e.g., BUNA N™) and preferably these materials do not contact the fluid or cells being cultured so as to reduce any potential toxic effects. However, the material does not have to be made of non-toxic material if the membrane restraint is not to come into contact with the cells of fluid media used for the culturing.

In the preferred embodiment shown in the drawings the bioreactor 100 includes two membrane members 30, each of the membrane members 30 including the gassing membrane that closes one side of one of the fluid chambers 20. It is to be understood, however, that the bioreactor 100 can include one membrane member 30, regardless of whether the bioreactor 100 include two fluid chambers 20. For example, one of the fluid chambers 20 can be closed by a plate or other component, such as a component that is not permeable to gas, while the other one of the fluid chambers 20 is closed by the membrane member 30.

The bioreactor 100 preferably includes a gassing chamber 40. The gassing chamber 40 can provide the gas that flows through the gassing membrane 30 to the chamber 20. As shown in the drawings, a preferred embodiment of the invention the gassing chamber 40 extends such that gas flows from a gassing chamber input 41 to a gassing chamber output 43, about parallel to a surface of the gassing membrane 30 through which the gas flows. When the gas flows parallel to the gassing membrane, the gas diffuses through the membrane perpendicular to the surface of that thin membrane. The gassing chamber 40 can also include a spacer to prevent gas flowing though the gassing chamber 40 flow flowing to an exterior of the bioreactor 100.

Preferably, the gassing chamber 40 is removably disposed in the bioreactor 100. Alternatively, the gassing chamber 40 can be immovably disposed in the bioreactor 100. It is preferred that the components of the gassing chamber 40 are manufactured from a transparent or translucent material, such that observation into the interior of the gassing chamber 40 is permitted.

In a preferred embodiment shown in the drawings the bioreactor 100 includes two gassing chambers 40, and the two gassing chambers 40 are disposed on opposite sides of the two membrane members 30. By this arrangement, the same or different gasses can be flowed through the gassing membranes to the two chambers 20. It is to be understood, however, that the bioreactor 100 can include one gassing chamber 40, or can omit the gassing chambers 40. When either or both of the chambers 20 that are closed by the membrane members 30 do not receive the gas from the gassing chamber 40, the bioreactor 100 can be disposed in a gaseous atmosphere that include the gas to be delivered to the chamber 20 through the gassing membrane.

Frame members 50 can be disposed on opposite sides of the above-discussed other components of the bioreactor 100, such that the components of the bioreactor 100 are held together and maintained as a single unit. Preferably, the frame members 50 are disposed on outermost surfaces of the two gassing chambers 40. The frame members 50 can be manufactured from a material suitable to evenly distribute a compressive force that holds other components of the bioreactor 100 to prevent undesired fluid or gas leaks there between. In one embodiment, the frame members 50 can be formed of metal, plastic, and/or mechanically stable materials and can be made of similar materials as the other members of the device provided it provides some structural integrity to hold the other components of the bioreactor together in alignment for use.

The frame members 50 can include one or more threaded voids aligned with a corresponding number of unthreaded voids. By this arrangement, one or more bolts can be disposed through the voids, such that threads on the bolts cooperate with threads in the voids, to connect the frame members 50 to one another. Alternatively each of the frame members 50 can include unthreaded voids, and cooperating sets of another embodiment, the frame members can be held together using clips or other suitable joining or fastening devices provided that such clips or devices suitably provide compressive force to hold the bioreactor components together in the proper alignment, e.g., in a manner that would prevent gas and/or fluid leakage. Combinations of these may also be employed.

The frame members 50, as are all the other above-discussed components of the bioreactor 100, are preferably formed from a material that is can be sterilized by one or more of radiation, steam and chemicals, and from a material that permits repeated reuse-by resisting corrosion or degradation.

It is to be understood that the bioreactor 100 optionally includes one or more seals, such as O-rings and the like, to provide desired gas or fluid tight corrections between or among the components of the bioreactor. Further, the components of the bioreactor 100 can include grooves, lips, protrusion, and the like to facilitate positioning of these seals.

Alternately, the individual components may be joined together and sealed by any of a number of methods for welding the parts together such as sonic, heat, and laser. In such embodiments, compressible sealing members and frame and bolt members may not be seeded. In another embodiment, the reactor body, sealing members, or other components can be constructed of flexible film material.

In one embodiment, a flexible, disposable fluid pathway containing one or multiple cell immobilization substrate(s) for a perfusion bioreactor system can be configured and used. This embodiment facilitates, a low-cost method of making the fluid pathway components compared to machined or molded components. The device in this embodiment can be maded of medical grade flexible films along with welding methods commonly employed with such materials to create the sealed fluid pathway (for the fluid and cell contacting parts). Medical grade silicone and other materials (e.g., TEFLON®) can be used. Such a device can the a single-use disposable and can be used with a outer-containing member that can be reusable made from modified non-fluid contact functional components, e.g., membrane restraint and gas chambers.

Modular perfusion bioreactor system with either 2-D or 3-D form capable of supporting multiple matrix/cell/tissue constructs.

The bioreactor 100 can be formed from a plurality of separable modules, including one or more of each of the scaffold 10, the fluid chamber 20, the membrane member 30, the gassing chamber 40, and other components, as described in detail above. Thus, it is to be understood that the structure is easily reconfigurable for the particular desired use of the bioreactor 100, as the desired modules are easily added or removed from the bioreactor 100 assembly.

The cells of the ex vivo generated tissue that can be obtained by culturing in the bioreactor described herein can, in certain embodiments, have enhanced proliferative potential and/or biological function. Such can be used in a wide variety of applications, including, but not limited to, therapy treatments including adoptive immunotherapy with effector cells, tumor specific cytotoxic T-cells, infectious disease specific cytotoxic T lymphocytes, cytokine induced killer cell therapy, antigen presenting cells to either tumor or infectious diseases, dendritic cells, antigen primed dendritic cells, tumor vaccines, genetically modified attenuated tumor cells, genetically modified antigen presenting cells, structural repair procedures such as cartilage defect repair, bone defect repair, tissue repair, wound healing, burn care, solid organ repair, neurological defect repair, etc. Derivation and expansion of antigen specific T-cell populations including, but not limited to, viral (e.g. EBB, HIP, CAM, HIV, influenza) and tumor reactive T-cells, ex vivo expansion of human tumor infiltrating lymphocytes (TILs) for adoptive cancer immunotherapy, derivation and ex vivo expansion of cytokine induced killer (CIK cells for rejection of human tumors including leukemia, lymphoma, breast and other cancers. Also, immunotherapy after autologous or allogeneic bone marrow transplantation. With dendritic cells; antigen presenting cell (APC)-based vaccines to stimulate I-cell responses in vitro or in vivo against simple or complex antigens including, but not limited to, tumor, viral fungal and bacterial antigens. Therapy may include treatment or prevention of disease in normal individuals or human cancer patients.

There are a variety of cell types that can be cultured in the device according to the present invention, including stem, progenitor, and terminally differentiated/mature cell types. Examples include stem cells (e.g., hematopoietic or stromal stem cells), progenitor cells (e.g., hematopoietic progenitors), mature myeloid cells, or stromal cells (e.g., from bone marrow). In another embodiment, the cells may be dendritic cells (e.g., myeloid- or lymphoid-derived) or non-myeloid mature cells which are other than stromal cells (e.g., the mature cells described above, especially T-cells or chondrocytes). Preferred cells which can be used include human hematopoietic cells, mesenchymal cells, dendritic cells, fibroblasts, hepatocytes, neural cells, epithelial cells, lymphocytes, keratinocytes, osteoblasts or osteoclasts. Specific examples of suitable human hematopoietic cells include megakaryocytes, monocytes, neutrophils, basophils, eosinophils, tumor specific cytotoxic T lymphocytes, cytokine induced killer cells, antigen presenting cells to either tumor or infectious diseases, dendritic cells, antigen primed dendritic cells, leukocyte precursor, and neutrophils. Suitable examples of mesenchymal cells include, chondrocytes, osteoblasts, myeoblasts, fibroblasts, tenoblasts, stromal cells (e.g., from bone marrow), tenocytes, adipocytes, osteocytes and myocytes. Suitable examples of lymphocytes include T-cells and B-cells. Pre-T and pre-B cells are also suitable. The T-cells ($CD3^+$) may be $CD8^+$ or $CD4^+$ cells, or cells derived from said populations. Mixtures of various cell types can also be used.

The cells may be obtained from a variety of sources using well-known techniques, see Heslop H E, Ng Cyc, Li C, Smith C A, Loftin S K, Krance Ra, Brenner M K, Rooney C M: Long-term restoration of immunity against Epstein-Barr virus infection by adoptive transfer of gene-modified virus-specific T lymphocytes. Nature Med 2:551, 1996; Lu P, Negrin R S: A novel population of expanded human CD3+ CD56+cells derived from T-cells with potent in vivo antitumor activity in mice with severe combined immunodeficiency. J immunol 103:1687, 1994; Roman; N, Gruner S, Brang D, Kampgen E, Lenz A, Trockenbacher B, Konwalinka G, Fritsch P O, Steinman R M, Schuler G: Proliferating dendritic cell progenitors in human blood. J. Exp Med 180: 83, 1994; Rosenberg S A, Spiess P, Lafreniere R: A new approach to the adoptive immunotherapy of cancer with tumor-infiltrating lymphocytes. Science 233:1318, 1986.

Culture media can be any known physiologically acceptable liquid culture medium, i.e., a medium which supports cell viability and proliferation under a variety of conditions. The composition of the media may vary with the cell type being cultured. Media suitable for culturing specific cells are well-known; for example, see Schmidt-Wolf I G H, Negrin R S, Kiem H, Blume K G, Weissmsn I L: Use of a SCID mouse-human lymphoma model to evaluate cytokine-induced killer cells with potent anti-tumor cell activity, J. Exp Med 174:139, 1991; Morse M A, Zhou L J, Tedder T F, Lyerly H K, Smith C: Generation of dendritic cells in vitro form peripheral blood mononuclear cells with granulocyte-macrophage-colony-stimulating factor, interlukin-4, and tumor necrosis factor-alpha for use in cancer immunotherapy. Ann Surg. July 1; 226:16, 1997; Romani N, Grunner S, Brang D, Kampgen E, Lenz A. Trockenbacher B, Konwalinka G, Fritsch P O, Steinman R M, Schuler G: Proliferating dendritic cell progenitors in human blood, J, Exp Med 180:83, 1994.

The culture medium contains organic and inorganic components required for Cell proliferation and may contain standard known medium components such as, for Example, AIM V, IMDM, MEM, DMEM, RPMI 1640. Alpha Medium or McCoy's Medium, which can use combinations of serum, albumin, cholesterol and/or lecithin selenium and inorganic salts. As known, these cultures may be supplemented with corticosteroids, such as hydrocortisone at a concentration of $10^{-4}$ to $10^{-7}$ M, or other corticosteroids at equal potent dose, such as cortisone, dexamethasone or solumedrol. The cultures are typically carried out at a pH which approximates physiological conditions, e.g., 6.9 to 7.4. The medium is typically exposed to an oxygen-containing atmosphere which contains from 4 to 20 vol. percent oxygen, preferably 6 to 8 vol. percent oxygen.

Illustratively, the medium used in accordance with the invention may comprise one or more basic components. The first component is a media component comprised of AIM V, IMDM, MEM, DMEM, RPMI 1640, Alpha Medium or McCoy's Medium, or an equivalent known culture medium component. The second is serum components which comprises at least horse serum or human serum and may optionally further comprise fetal calf serum, newborn calf serum, and/or calf serum. The third component is a corticosteroid, such as hydrocortisone, cortisone, dexamethasone, solumedrol, or a combination of these, preferably hydrocortisone.

The compositional make up of various media which can be used in the present invention are well-known, see U.S. Pat. No. 5,635,386, columns 11-30; Lewko W M, Good R W, Bowman D, Smith T L, Oldham R K; Growth, of tumor derived activated T-cells for the treatment of cancer. Cancer Biotherapy, vol. 9, No. 3, pp 221, 1994; Freedman R S, Tomasovic B, Templin S, Atkinson E N, Kudelka A, Edwards C L, Platsoucas C D: Large-scale expansion in interleukin-2 of tumor-n infiltrating lymphocytes from patients with ovarian carcinoma for adoptive immunotherapy: J. Immunol Methods 167:145-100, 1904.

The serum component, if used, may be present in the culture in an amount of at least 1% (v/v) to 50% (v/v), The serum concentration may also be approximately 10 to 30% (v/v). The third component may be present in an amount of from $10^{-7}$ M to $10^{-4}$ M, and can also be present in an amount of from $5\times10^{-6}$ to $5\times10^{-5}$ M. The media component represents the balance such that all three components add up to 100%. Alternatively the serum component can be replaced by any of several standard serum replacement mixtures which typically include insulin, albumin, and lecithin or cholesterol. See, Migliaccio, et al, Exp. Hematol. (1900) 18:1049-1055, Iscove et al, Exp. Cell Res. (1983) 126:121-126, and Dainiak et al, J. Clin. Invest, 76:1237-1242.

The cells can be added to the culturing device and in methods of culturing cells at varying densities. In one embodiment, the cell density can be from about $10^4$ to $10^8$ cells per ml of culture. In alternative embodiments, the cell density is $5\times10^4$/ml to $2\times10^6$/ml. In another embodiment, the local cell density can approach or exceed $10^9$ cells/ml.

In another embodiment the culture media can also contain various growth factors (e.g., hematopoietic growth factors), including synthetic hematopoietic growth factors. The types of and combinations of growth factors can be selected according to the nature of the specific cell type or cell types being cultured. Examples of such growth factors include, GCSF, GMCSF, interleukins such as IL-2, IL-6, IL-12 and others, Tumor necrosis factor (TNF), interferons (IFN α, β, or γ) and others. The particular growth factors which stimulate a given cell type in cell culture are well-known, see for example, Romani N, Gruner S, Brang D, Kaampgen E, Lenz A, Trockenbacher B, Konwalinka G, Fritsch P O, Steinman R M, Schuler G: Proliferating dendritic cell progenitors in human blood. J. Exp Med 180:83, 1994; Maraskovsky E, Brasel K. Teepe M, Roux E R, Lyman S D, Shortman K, McKenna H J: Dramatic increase is the number of functionally mature dendritic cells in Flt3 ligand-treated mice: multiple dendritic cell subpopulations identified. J. Exp Med 184:1953, 1996; Sallusto F, Lanzavecchia A: Efficient presentation of soluble antigen by cultured human dendritic cells is maintained by granulocyte/macrophage colony-stimulating factor plus interleukin 4 and down-regulated by tumor necrosis factor alpha, J. Exp Med 179:1109, 1994; Santiago-Schwartz F, Divaris N, Kay C, Carsons S E: Mechanisms of tumor necrosis factor-granulocyte-macrophage colony-stimulating factor-induced dendritic cell development Blood 82:3019, 1993; Siena S, Di Nicola M, Bregni M. Mortarini R, Anichini A, Lombardi L, Ravagnani P, Parmiani G, Gianni Am: Massive ex vivo generation of functional dendritic cells from mobilized CD34+blood progenitors for anticancer therapy. Exp Hematol 23:1463, 1995; Rosenberg S A, Spiess P, Lafreniere R: A new approach to the adoptive immunotherapy of cancer with tumor-infiltrating lymphocytes. Science 233:1318, 1986; Rosenberg S A, Packard B S, Aebersold P M, Solomon D, Topalian S L, Toy S T, Simon P, Lotze M T, Yang J C, Seipp C A, Simpson C, Carter C, Bock S, Schwartzentruber D, Wei J P, White D E: Use of tumor-infiltrating lymphocytes and interleukin-2 in the immunotherapy of patients with metastatic melanoma. New Engl J. Med 319:1676, 1988; Schmidt-Wolf I G H, Negrin R S, Kiem H, Bluime K G, Weissman I L; Use of a SCID mouselhuman lymphoma model to evaluate cytokine-induced killer cells with potent antitumor cell activity. J. Exp Med 174:139, 1991.

IL-2 can be used for culturing T-cells. The amount of IL-2 is the culture medium may vary widely, for example, the IL-2 concentration can be 25 to 1,000 IU/ml. GM-CSF, IL4, TNf-α, Flt3-L, or combinations thereof, can be added to the culturing medium when expanding dendritic cells. General concentration ranges for cytokines in dendritic cell culture media are: GM-CSF: 50 ng/ml (1 to 500 ng/ml); IL4: 25 ng/ml (1 to 500 ng/ml); TNF∝25 ng/ml (1 to 500 ng/ml); Flt4L; 25 ng/ml. (1 to 500 ng/ml). These ranges include all specific values and subranges there between.

Other growth factors which may be added to the culture medium include the cytokines IL-3 and GM-CSF alone or together at a rate of from 0.1 to 100 ng/ml/day, preferably about 0.5 to 10 ng/ml/day, most preferably 1 to 2 mg/ml/day. EPO may be added to the nutrient medium is an amount of from 0.001 to 10 U/ml/day, preferably 0.05 to 0.10 U/ml/day. Mast cell growth factor (MCGF, e-kit ligand, Steel factor), may be added to the medium in an amount of from 1 to 180 ng/ml/day, preferably 10 to 50 ng/ml/day IL-1 (α or β) may also be added in an amount of from 10 to 100 units/ml per 3 to 5 day period. Additionally, IL-6, G-CSF, basic fibroblast growth factor, IL-7, IL-8, IL-9, IL-10, IL-11, PDGF, or EGF may be added, at a rate of from 1 to 100 ng/ml/day.

The liquid culture medium used in culturing cells can be perfused, either continuously or periodically to enhance the growth, the proliferative potential and/or biological potential of the cells cultured in the bioreactor device. The rate of medium replacement may be at least 25% daily replacement, at least 50% daily replacement and may be 25% to 100% daily replacement for a local cell density of from $1\times10^4$ to $1\times10^7$ cells per ml of culture and up to shout $10^9$ cells per ml of culture. This rate can be adjusted for other cell types if desired. In one embodiment, the replacement rate is relatively low at the beginning of the culturing and then increased as the cell density in the culture increases.

In certain embodiments, cells being cultured can be subjected to varying shear forces of the media passing through the matrix material and, perhaps, coupled with varying dimensions of the matrix material itself. By controlling both the dimensions of the matrix material, e.g., spacing of gaps between fibers of a nom woven or woven material, and/or varying shear conditions (e.g., media flow) the Inventors have observed that the same cell population can be driven to produce more predominant cells of one type compared to another cell type.

In some embodiments a pulsed flow medium delivery can be used to facilitate cultured cells and the generation of tissue-like structures within the bioreactor. Generally, such pulsed flow medium delivery involves a start and stop of the medium delivery and while perfusing the medium on the cells a portion of the used medium is recycled (or all of the medium can be recycled as well) while adding fresh medium to maintain cytokines, growth factors, and other agents produced by the cells is the culture so as to maintain a suitable local environment for cells being cultured.

In some embodiments, fluid volume being provided can be 20-40 mL of media/$25 \times 10^6$ cells seeded into the system, for the first 14 days, then can be increased 45-60 mL as the culture expands. In certain embodiments, a recirculation flow rate of 3 L/minute at 60 rpm and volume exchange rate of % void volume every 30 minutes is preferred.

When compared to static 3-D cultures at the same seeding density, cells in the perfusion bioreactor having a three dimensional matrix of cells maintain a higher viability is long term (45+ days) culture (60-90% 2-D vs. 90-99% 3-D).

The gas mixture for standard cultures is 5% $CO^2$, 20% $O^2$ and 75% $N^2$. It is well known that stem cells prefer lower oxygen tensions, therefore a strategy where the concentration of oxygen in the mixture is started at a lower concentration, for example 2-5%, and then can be increased as the culture progresses to the 20%. As the density of tissue increases, the local concentration of oxygen deep within the matrix may remain at near hypoxic conditions, even though the concentration within the gas chambers is increased.

Additionally, the 5% $CO^2$ can facilitate pH maintenance early in the culture, but may be reduced to 1-2%, or even zero % as the culture starts to actively metabolize. In late stage cultures, removal of excess $CO^2$ from the media can sometimes be problematic.

The flow rate of the mixed gasses may or may not be precisely controlled, and generally it is not necessary to do so. However, the flow rate of the mixed gases is preferably targeted to be at or above the metabolic requirements of the culture. This rate is set as a slow bubbling through a humidifier, which minimizes the removal of small amount of water vapor that can transit the gassing membrane. Alternately, a small aquarium-type pump can be used to pump can be used to pump the mixed environment from the incubator, rather than from a tank of mixed gasses or from a precise gas mixing system from tanks of the purified individual gasses through the gas chambers.

A variety of media can be used depending on the types of cells being cultured and the types of cells that develop over the period of the culture. As described hereinabove, one will recognize that the media can be changed over the course of the culture to meet the nutritional requirements of the cells being cultured and/or to facilitate the development of certain types of tissue-like matrices. Combinations of media can also be used at a single time.

One type of media used in culture includes IMDM (Iscove's Modified Dulbecco Media) supplemented with 10% Fetal Calf Serum (FBS), 10% Horse Serum, 0.25 ρM Hydrocortisone, 5 μg/ml Gentomycin, and Growth Factors added before use such, as Thrompoietin (Tpo) at 10 ng/ml final concentration, Flt-3 Ligand (FL) 25 ng/ml final concentration.

Another example of a medium that can be used, for example, for culturing T-cells is a 50/50 mixture of AIM-5 and RPMI supplemented with 10% Human AB serum plus the addition of OKT-3 at prescribed time points. Depth filtration may or may not be performed after the cells have been seeded using only laminar fluid flow. Lactate levels can be kept few.

If the cells are rapidly expanding the cells can be harvested frequently.

In some hematopoietic applications, we have found that by inducing the "depth filtration" shear, we can induce B cell formation from ficolled inoculums and sustain the populations for prolonged periods of time.

The metabolic product level in the medium is normally maintained within a particular range. Glucose concentration can be maintained in the range of about 5 to 20 mM. Lactate concentration is usually maintained below 35 mM, preferably below 0.5 mg/ml. Glutamine concentration is generally maintained in the range of from about 1 to 3 mM. Ammonium concentration is usually maintained below about 2.4 mM. These concentration may be monitored by either periodic or on-line continuous measurements using known methods. See e.g., Caldwell et al, J. Cell. Physiol. (1991) 347:344-353.

Culture conditions should be optimized for any cell/tissue being grown and may be different for the purposes of the research or clinical application. This culture bioreactor allows conditions to be changed easily, e.g., flow rate of nutrients, continuous or pulsatile flow, gas mixture, nutrient gradients, etc.

The culture time may vary widely. The cells are preferably cultured for at least the minimum amount of time required to produce cells with enhanced replicative potential, biological function, or both. This time may vary with cell type, depending on the cell doubling time. In one embodiment, the cells are cultured for at least 2 days, at least 4 days, etc. The maximum culture time is not particularly limited. For example, the cells may be cultured for up to 10 days, up to 25 days, up to 50 days, up to 75 days, up to 100 days, up to or more than one year, etc.

After culturing the cells to generate a tissue-like structure in the bioreactor as described herein, the cultured cells and/or the tissue-like matrix may be isolated by harvesting them from the culture apparatus. The cells may be harvested by, for example, withdrawing the cells by syringe, or by continuously allowing the cells to flow out of the culture reactor, by the pressure produced by replacing the culture medium, through an exit tube. In addition, or alternatively, the ex vivo generated tissue-like matrix can be removed from the bioreactor, in whole or parts thereof, and implanted into a patient at the desired location (or locations). After harvesting, the cells may be infused in a patient to obtain the therapeutic benefits of the cultured cells. In another embodiment, the cells and/or ex vivo generated tissue matrix can be to investigate interactions between the cells in the matrix, used to study the effects on various drugs, therapeutics or other agents on the structure and/or function of the cells in the ex vivo generated tisane matrix.

Therapeutic benefits include generating tissue in a patient, such as any of human bone marrow, human blood, human immune system, human bone, human cartilage, human vascular tissue, human muscle, human pancreatic cells, human nerves or human epithelial tissue and others. The procedures for infusing the cells and implanting cell matrices like the ex vivo generated tissue of the present invention for human therapy are well-known.

Optimum protocols and dosages of cells and/or the ex vivo generate tissue matrix used for various therapies will vary according to the therapy being sought, the patient's age, physical condition and other relevant medical criteria. The cells can be infused directly into the patient, e.g., intravenously or parenterally or locally as well as surgically implanted into one or more desired locations in the body. The cells can be provided by themselves in a suitable delivery solution and/or coupled with one or more types of carrier or matrix materials, preferably those that are biodegradable in the patient's body.

Having generally described this invention, a further understanding can be obtained by reference to certain specific examples which are provided herein for purposes of illustration only and are not intended to be limiting unless otherwise specified.

EXAMPLES

Example 1

An example of a bioreactor and its use is described below.

Materials

Bioreactor Parts include: Upper Polycarbonate Bioreactor Body w/integrated fittings. Lower Polycarbonate Bioreactor Body w/integrated fittings, Matrix-BARD 1642, Atex 3618, Polycarbonate Membrane Support, Polycarbonate Top Clear Cover, Stainless Steel Luer Needles with Plastic Luer Connect, Teflon O-Ring, Stainless Steel Nutplate, Stainless Steel Clamp Ring, Screws, and FEP Film.

A flow Loop can be set up using Value Plastic and Qosina polycarbonate luers, Cole Palmer Pharmed Tubing 96900-04, Cole-Palmer Orange/orange Pharmed three-stop tubing 95708-26, Glass Buffer-Superior Glass Blowing, Cole-Palmer Syringe Filters 02915-22, A gas mixture of 5% $CO^2$, 20% $O^2$ and 75% $N^{2.}$ can be provided. The mixed gas flow need not be precisely controlled, but targeted as a slow bubbling through a humidifier. Alternately, a small aquarium pump can be used to pump can be used to pump the mixed environment from the incubator through the gas chambers.

Fluid flow can be controlled by a peristaltic pump. The fluid flow is can be set to exchange from 0.8 ml pulsed per 30 minutes up to 1.75 ml pulsed per 30 minutes. During days 5-14 the media volume of the flow loop can be 50% exchanged. Higher flows and a higher percentage media exchange may be required for active metabolizing cultures, using a strategy to keep the visual pH near physiological ideals by more frequent pulses and a higher flow loop volume exchange daily. Lactate preferably should not be allowed to exceed 1.2 moles per liter for most tissues.

Before priming the system, cheek to make sure that the all of the plastic flow loop lures and the bioreactor screws are tightly sealed. Place the media vessel above the system to allow hydrostatic pressure to aid in priming. Clamp off every outlet of the media except for the outlet containing the air filter and the line leading to the media/feed line. By clamping off the lines, unnecessary pressure will not enter the bioreactors and tug on the gassing membranes.

Attach a large 60 or 30 cc syringes to the air filter using the provided adapters. Pull the syringe, so media is encouraged to flow into the buffer. When the fluid volume reaches the red mark near the first side port, stop pulling and remove the syringe. Remove the clamps from the bioreactor and allow the fluid to naturally flow into the bioreactors and remaining tubing. Connect the stop tubing lines to the pump and turn the pump on. Clamp off the media line. While the system is circulating, and the bioreactors are filling, hold the bioreactor upright at a 90 degree angle. You will be able to see the bioreactors fill with media. When the last air bubble leave, place the bioreactors back down on the level surface and check for any leaks in the system. If everything is normal, let the system circulate for one hour. Clean up and media residue from leaks with paper towel and generous amounts of ethanol. After one hour, detach the lined from the pump and turn the pump off. You are now ready to seed the system.

After the bioreactor system has been primed, and no leaks have been established, place the bioreactors on a flat and level surface below the buffer vessel in the incubator (180 degree angle). Make sure that all the gas lines are connected and there is gas flow. This will prevent disruption of the attaching cells post seeding. Once all manipulation are completed, check to make sure that there are no air bubbles.

Obtain a 3 or 5 mL syringes and 16-20 gage needles. Attach the needles to the syringes and aseptically pull 3.5 ml of system media and cells. When using light density bone marrow mononuclear cells, a seeding density of 33,000,000 can be used. Try to pull and small bit of air into the syringe when the 3.5 ml of media is obtained.

Check to sec that no sir bubbles are in the tip of the syringe. Disconnect the needle and attach the syringe to the harvest port of the bioreactor located on the upper back of the bioreactor. Place a clamp behind the harvest port so that when the syringe is depressed, fluid can only be directed into the bioreactor. Slowly depress the syringe and force the cell suspension into the bioreactor. When the media has cleared (visible through the "T" at the harvest port) watch for the air to "chase" the media through. As soon as the air bubble has crossed the "T", clamp off the harvest port. Remove all clamps and allow the system to sit undisturbed for one hour.

After one hour, place a clamp on the top port of the back of the bioreactor (the harvest port line), and one clamp on the bottom inlet line (the harvest line). Both lines that contain ports should now be blocked off. Follow the two remaining lines to the pump and connect these lines to the pump. Turn the pump on for one minute, allowing fluid to come in from the top of the front of the bioreactor and leave out the back of the bottom of the bioreactor. This forces the cells to "depth filtrate" through the entire matrix. After one minute, turn the pump-off and disconnect all lines to the pump. Remove all clamps, and allow the system to sit undisturbed for 48 hours.

At the end of 48 hours, put the bioreactors at a 45 degree angle. Connect all lines to the peristaltic pump and turn the pump on to the regular dosing mode. Regular harvests can now be taken beginning on day 4 post seeding.

After the fourth day post seeding, regular daily harvests can be taken. Try to take a harvest about 30 minutes post circulation to allow the cells to settle in the bottom of the bioreactor. Detached the circulation lines from the pump and wait for the appropriate amount of time before harvesting. Place a clamp behind the harvest line in the front of the bioreactor so fluid can only be pulled from the bottom of the bioreactor. Place clamps on both of the top line of the bioreactor so fluid is not pulled throughout the matrix depth. Attach a 5 or 10 cc syringe to the harvest port and pull 3 ml slowly into the syringe. If the culture is more than 14 days old and/or extremely metabolically active, it may be necessary to pull 5 mol from the system. Clamp off the harvest port, remove the syringe, sod replace the cap after spraying everything with ethanol. Analysis can be done on removed media after the system has been refilled.

To refill the buffer, place clamps on every outlet of the glass buffer except the media line and the air filter line. Attach a large 60 or 30 cc syringes to the air filter using the provided adapters. Pull the syringe, so media is encouraged to flow into the buffer. When the fluid volume reaches the red mark near the first side port, stop pulling and remove the syringe. Remove the clamps from the bioreactor and allow the fluid to naturally flow into the bioreactors and remaining tubing.

Connect the stop tubing lines to the pump and turn the pump on. Clamp off the media line. Cultures can be harvested every 2-3 days.

To terminate a culture, first detach the circulation lines from the pump. If a regular harvest is to be taken, it should be conducted next. To remove the bioreactors, clamp off every line before and after the plastic lures leading to the bioreactor. Unhook the bioreactor and carefully carry to a laminar flow hood. Hold the bioreactor above a 50 cc centrifuge tube and unclamp the top and bottom flow loop lines, allowing the bioreactor contents to drain into the tube. The harvest will contain some loosely adherent and well and non adherent cells, so cell counts, viabilities, morphologies, and molecular marker s may very slightly different than the regular daily yields.

Disassemble the bioreactor and carefully remove the fabric matrix with sterile scissors and place it in a sterile dish with some prewarmed media or PBS pending further manipulation. Follow protocols for SEM, confocal, live/dead staining, fixation, and or enzymatic harvest described in the protocol manual. Discard and clean bioreactor and flow loop pieces as listed in the sanitation section of the protocol manual.

After the terminal harvest, the bioreactor in whole, or in part, can be disassembled and sanitized for reuse.

To create the shear condition, the bioreactors were subjected to a permanent "seeding depth filtration". This is done by placing a clamp outside both harvest and seeding port lines so the fluid is forced to come in from the top of the bioreactor and flow through the matrix out to the bottom when circulating. This condition puts a mechanical shear force on the culture every time it circulates.

By changing the flow rate, a culture can change dramatically. Increasing a flow rate may be recommended for cultures that appear exceptionally metabolically active.

More frequent harvesting may also be recommended if a culture metabolizes quickly and more frequent circulation appears to have little improvement.

Example 2

Experiments were designed using the 3-D perfusion bioreactors incorporated into a recirculating flow loop with a minimum of two reactors per flow loop. The components of the loop were connected using biocompatible tubing from Pharmed®. A peristaltic pump was used to recirculate media, also using Pharmed pump tubing. A custom made glass flow-through vessel was used in each flow loop to both increase the loop media volume and optionally, provide a secondary means for released cells to settle and be removed from the circulating media.

The tissue culture media (LTBMC) used in each of these examples was a Formulation designed for the long term culture of bone marrow derived cells. This formulation used an IMDM base media supplemented with serum, hydrocortisone and growth factors. The media has been used widely by those culturing stem cells from bone marrow.

Example 2A

The purpose of the experiment was to compare how both, the source of fabric and methods of construction of that fabric affect the outcome of the culture.

Figure 2:
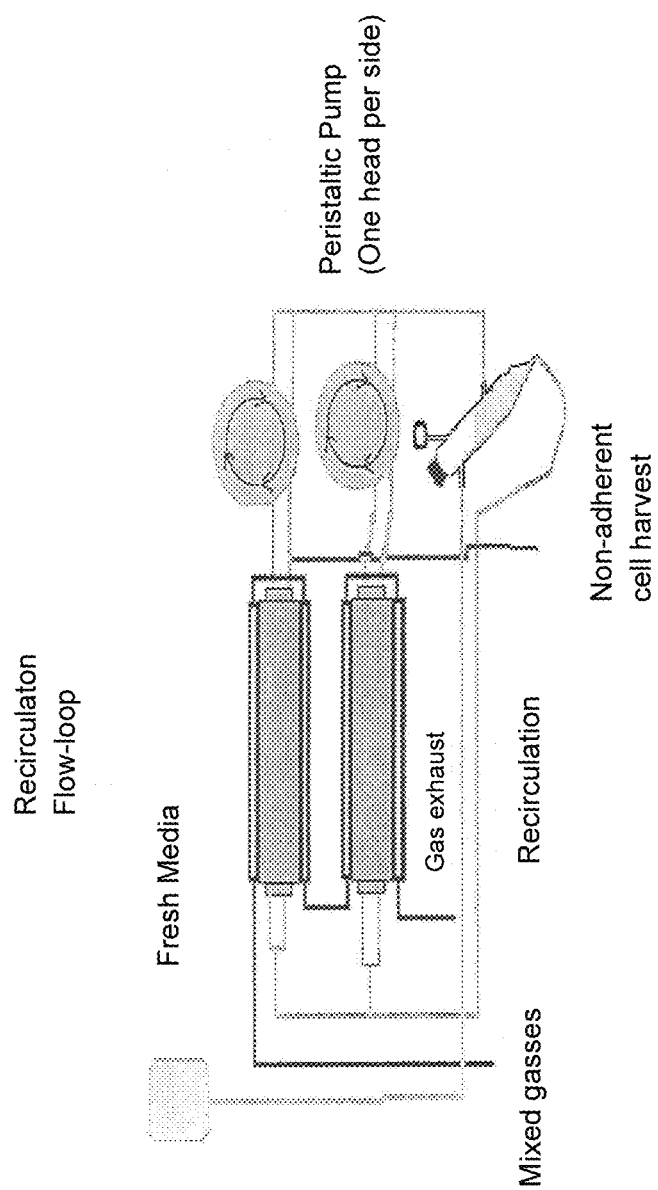
FIG. 2 is a depiction of a design for a recirculating flow loop described in the Examples.

Eight bioreactors were set up in 4 flow loops, 2 bioreactors per flow loop. Each flow loop contained a different matrix [F2 matrix, B-T1, B-tk2, and A1]. Nutrient media was recirculated in each flow loop using a pulse flowrate of ½ bioreactor volume every 30 minutes. See experiment design in FIG. 2.

Beginning on day 4, three ml, of media and cells were harvested tri-weekly (Tues, Thurs, Sat) from the bioreactor and analyzed for cell count, viability and lactate accumulation. Less frequent analysis of cellular morphology, differential cell analysis using the Coulter AcT, colony assays and flow cytometry was completed.

On day 18 one bioreactor of each flow loop was harvested for microscopic analysis and to provide a tissue sample for implantation into to immune compromised mouse to look at engraftment competence of the cultured tissue. Media and cells was drained from each bioreactor and given to flow cytometry for the evaluation of surface markers as a determination of cell types released. The remaining bioreactor from each variable was continued in culture to look at the comparative longer term viability and productivity of bioreactors using these various fabrics.

The warmest was terminated on day 93. Bioreactors were drained for analysis of the released cells, disassembled to remove the matrix/tissue construct, which was fixed and prepared for microscopic examination. Samples of each matrix/tissue construct were examined using a live/dead stain, confocal imaging of surface markers and by SEM.

The day 18 harvest of the bioreactor showed a lower viability, but higher cell yield in the sloughed cells from the F-2 bioreactor when compared to the other matrix samples. Cell number and degree of normal morphological development was depressed on this matrix as compared to the control culture.

Implantation of a small piece of this matrix/tissue construct from the reactor with the A-1 matrix into the peritoneum of an immune compromised mouse resulted in definite engraftment, with human hematopoietic cells seen in the bone marrow and in circulation in the mouse.

Microscopic analysis of the matrix from the terminal harvest on day 93 revealed that cells had infiltrated the depths of the matrix on all samples. Confocal microscopy revealed distinct handing patterns throughout the matrix supporting that different cell population had infiltrated the depths of the matrix. The SEMs from this experiment support that the cells aggregated throughout the matrix depth on all fabrics, although differences in cellular attachment to the fibers could be observed. Cells were more spread out on the F-2 material and produced more ECM, while cells produced less ECM and aggregated in more natural clusters of cells or boluses in the other materials.

Example 2B

This experiment was designed to look at the effects of fluid shear on tissue development and cellular differentiation in the 3-D bioreactor system. Cells and tissue experience little fluid shear is a normally operated 3-D bioreactor of this design. Media flow is parallel to the matrix and developing tissue, thereby exerting only minimal shear to the cells on the surface of the matrix. Shear can be generated in the tissue by diverting a portion, or all of the media to flow through the more open pores of the matrix/tissue construct. Data from previous studies had suggested that cultures exposed to fluid shear in the 3-D matrix of our systems yield a higher proportion of B and T cells lineages in the sloughed cell harvest.

Two recirculating flow loops, each containing two bioreactors, were setup in parallel to further investigate this finding. After 21 days of culture, one set of bioreactors was clamped so that media was forced to enter into the top of the bioreactor, flow through the matrix and exist out of the bottom, creating a constant "cross-flow" in the system. Prior to the introduction of shear, both systems utilized the normal media perfusion parallel, above and below, to the matrix and developing tissue.

The diagram in FIG. 3 schematically depicts the cross-flow generation of fluid shear in the 3-D bioreactor design.

Each bioreactor was seeded with 33.3 million normal human BMMC's from a commercial source. Two million cells were given to flow cytometry for an analysis of the inoculums as a base-line, as there is a significant donor-to-donor variability. Normal circumfusion flow was initiated 48 hours following the cell seeding steps.

On Day 4 harvest of normally sloughing cells was started. Approximately 500,000 cells were collected from each loop containing 2 bioreactors. Viability of the collected cells was over 98%, with cells appearing morphologically normal.

Released cells were harvested three times weekly from each bioreactor and analyzed for viability and cell count. Lactate analysis, Flow cytometry, colony assays, cytospins, and diff counts were regularly preformed on the cell harvests.

The viability of the harvested cells remained in the high 80%'s and cell harvests continued to yield about 500,000 cells per flow loop through the initial stages of this experiment.

On day 21 a released cell harvest of the systems was completed prior to the flow configuration change. A sample was given to flow cytometry as a baseline for this experiment. A flow generated shear as above was introduced to the cultures in flow loop A. Nutrient flow was diverted from a parallel path to the culture (where shear is minimal, except at the culture surface), to a flow where the nutrient was forced through the matrix/tissue construct in a cross flow mode.

Prior to the introduction of the fluid shear each flow loop (2 bioreactors) was yielding slightly less than 1 million cells at 85% viability. At 48 hours after this change, there was a dramatic increase in the number of cells collected from the cross flow loop.

A terminal harvest was performed on all bioreactors from this experiment at day 136. Bioreactor drains were conducted and cells were analyzed per protocol. Matrices were stained by Live/dead staining and were fixed per protocol in Gluteraldehyde and taken to and imaged at an outside laboratory. These samples were stained with antibody conjugated to an Alexaflour Fluorochrome. Enzymatic Harvest were also performed on one matrix of both Loop A and B, but despite high cell counts, Live Dead staining of the matrices suggested that many cells still remained to attached to the matrix even after typsinization.

Before the introduction of sheer, all flow loops produced a normal flow profile, a viability of near 98% on regularly harvested cells, and yielded 500,000+ cells in each daily harvest. Alter the introduction of shear, the cultures with induced shear produced 1 million+ cells in each harvest at a 75%+ viability, while the no shear loop remained unchanged.

The flow profile, as determined by forward scatter from the bioreactors with shear show a definite myeloid population, which is absence in the flow loop without shear. Without shear, a larger T-cell subset population is seen. The CD34+ population also appears higher at nearly 2% after four weeks. Anybody specific staining with confocal was only achieved successfully on Loop A, however a significantly high CD34+ was observed o the matrix, with the 34+ cells being very closely associated to stromal cells and ECM. The remaining cell markers showed cells scattered throughput the matrix depth, which was supported by the projected images taken from a matrix scan. Selected images can be seen following this report.

Data gathered from cytokine assays also support functionality. These results suggest that inducing sheer can be an effective way of increasing cell yields, reducing myeloid cells and increasing lymphoid and progenitor subsets.

Flow cytometry showed a dramatic difference in the two flow loops of this experiment before and after stress. This data was compared to another experiment that examined high and low density matrix that had been subjected to periods of nutrient deprivation (flow interruption), another form of stress. This allowed us to draw conclusion about our system 1) Over time, 2) Between high and low density matrices, 3) Between each type of stress and their control, 4) Between the two types of stresses.

The flowing chart illustrates some of the cell surface profiles, characteristic of differing cell types, observed see under specific induced conditions.

| Sample | # Days | % Lin-CD34+ | % CD34+ | % CD41+ | % CD14+ | % CD19+ | % CD3+ | % CD16+ | % CD4+ | % CD8+ |
|---|---|---|---|---|---|---|---|---|---|---|
| Inoculum Low Density | 0 | 2.73 | 3.54 | 2.03 | 5.19 | 14.84 | 30.5 | | | |
| Pre-Stress Low Density | 18 | 0.9 | 1.42 | 0.33 | 12.13 | 0.89 | 22.82 | 2.63 | | |
| Post-Stress High Density | 25 | 0.97 | 1.65 | 4.3 | 27.7 | 23.14 | 15.06 | 25.06 | | |
| Pre-Stress High Density | 18 | 0.72 | 0.96 | 0.39 | 21.13 | 1.07 | 24.63 | 3.75 | | |
| Post-Stress | 25 | 0.04 | 0.34 | 4.52 | 2.25 | 60.95 | 9.22 | 3.74 | | |
| Run #27 Stressed with Introduction of Sheer | | | | | | | | | | |
| Inoculum Low Density | 0 | 5.73 | 3.46 | 1.59 | 4.71 | 9.8 | 16.48 | 18.01 | | |
| Pre-Stress Low | 30 | 1.11 | 0.5 | 0.69 | 41.02 | 1.42 | 2.61 | 12.62 | | |

-continued

| Sample | # Days | % Lin-CD34+ | % CD34+ | % CD41+ | % CD14+ | % CD19+ | % CD3+ | % CD16+ | % CD4+ | % CD8+ |
|---|---|---|---|---|---|---|---|---|---|---|
| Density Post-Stress Low Density Control | 51 | 1.1 | 0.02 | 6.7 | 44.22 | 24.11 | 3.23 | 12.12 | 40.52 | 4.56 |
| Pre-Stress Low Density Control | 30 | 1.6 | 1.33 | 1.79 | 51.81 | 1.21 | 1.69 | 15.83 | | |
| Post-Stress | 51 | 1.8 | 0.39 | 4.79 | 70.41 | 0.08 | 1.34 | 32.4 | 70.26 | 0 |

Note:
Control was not stressed

Differences over time reveal more myeloid cells, fewer B and T cells. When subjected to constant conditions of shear, myeloid populations decrease and B and T cell subsets increase. Fabrics produced from more dense yarn yield more monocytes. When circulation is interrupted, there is an increase of myeloid, B and t cells with higher density fabrics in this condition resulting in more B cells (approx. 60%) and lower density fabrics in this condition yielding more monocytes and a 20% increase in B cells.

Example 3

The purpose of this experiment was to compare matrix materials with and without the presence of a silver ion in both modified recirculating flow loops as well as in a set of bioreactors within a single pumphead flow layout. Additionally, a modified flow loop was designed to be housed within an incubator to investigate the feasibility of using another support platform. Materials include bioreactors disposable dispensing needles glued into the bioreactor bodies with Dymax 1180-M adhesive, Pharmed tubing, small size glass buffers from Superior Glass Blowing, and matrix fabric from both Foss Manufacturing end Atex (Foss Ag(−) and Ag(+) matrices, and Atex 3618 matrices.).

Five separate flow loops were built on two Opticell™ shelves with a standard MR layout except for the single drive layout where the perfusion flow was looped through the bioreactor, rather than with a separate pumphead moving the media in parallel across the matrix in the bioreactor. Both shelves were autoclaved per standard procedure. Two bioreactors with Ag+ matrix were inserted in a modified flow loop with single head drive as above. Four other bioreactors (two flow loops) also had Ag+ matrix, one set in a modified loop operated in an incubator, and the second set as control operated is the Opticell™ unit. Two additional modified flow loops were assembled on the Opticell™ shelf one with bioreactors containing Ag (−) Foss matrix and one with a thick woven Atex 3618 matrix.

The flow loops were filled with media allowed to condition for about two hours, and then seeded with 25 million BMMC's obtained from Poetics #1784A. Controls were set up in 4 wells of a 12 well plate. Each well had 2 mL of complete DARPA media. Two wells contained Foss non-woven fabric with a silver ion while the other two had no matrices.

After seeding into the bioreactor, cells were allowed to settle into the matrix before depth filtration. After depth filtration was completed the pump was then turned off to allow the bioreactors to sit until day 4 when flow was initiated.

Beginning on day 6 samples of media containing sloughed cells were removed from the lower chamber of each bioreactor (ran at a 45 degree angle) and a cell count was preferred. This procedure was repeated three times per week. Cells taken out were analyzed by cell and viability counts, lactate analyses, colony assays, diff counts, dissolved oxygen readings, cytospins, and flow cytology. Almost daily, the single pump system bioreactors had to be refilled due to bioreactor draining. Before cell harvests were taken, the system was allowed sit for one hour after being sampled.

On day 32, a terminal harvest was done on both Single Pass bioreactors and on one Ag (−) bioreactor. The terminal harvest followed standard protocol for a bioreactor drain, except that an additional 15 mL of DARPA media was pushed in a cross flow manner through the matrix after the normal bio drain was completed. This media was combined with the bioreactor drain media. A cell and viability count was done on the resulting cell pellet after resuspend in culture media. All of the matrices were subjected to typsinization with a spinner flask and then live dead stained.

On day 34, all of the bioreactors except for the 3618 bioreactor were terminated. On day 61 one of the 3618 bioreactors was removed in order to investigate the level of cell growth that was contained within, the bioreactor and matrices at the 60 day time point. A cell count and viability, as well as a flow analysis were preformed an cells recovered from the bioreactor drain. Inlet and outlet matrices were assessed by confocal/live-dead stain/SEM analysis.

Despite robust cell growth, a terminal harvest was done on the remaining bioreactor on day 110 to gather more data Matrices pieces were assessed for implantation into immune compromised mice to determine hematopoietic reconstitution potential of the cultured marrow, as well as samples of the cultured matrix sent out for confocal, SEM, and further tissue staining. Cytospins, colony assays, diff counts, cell and viability counts were done on the cells recovered in the bioreactor drain. The bioreactor body was stained to visualize any cells that had attached to the bioreactor itself. Additional media was saved for further analysis and PCR.

The terminal harvest of the first bioreactor containing the Atex 3618 woven matrix revealed a large number of healthy cells from the bioreactor and within the matrix. A live/dead stain of a matrix disc following a bioreactor drain exposed many viable cell clumps at the woven fabric junctions and with most cells prevalent deep within the matrix rather than at the surface.

The yield of sloughed cells and cell viability from the normal bioreactor harvests were declining prior to the pump tubing rupture during the run. This failure precipitated a change to cross flow media perfusion, after which both the viability and cell counts improved drastically.

As a result of the tube rupture and switch to cross flow, new DARPA media was introduced. Several buffer volumes were exchanged over the ensuing week resulting in an improvement in both the cell yield and viability. Cell morphology was slightly different than what was witnessed in previous runs. Typically, cells appeared to grow and differentiate into larger cells by the 10-14$^{th}$ day of culture. In this run, especially following the switch to cross-flow, cells observed in the bioreactor drains appeared as small cells, similar to the size of CD 34+ cells. Colony assays yielded few macrophage colonies and many granulocytic colonies. This is the reversal of what has been typically observed in previous cultures.

The terminal harvest at day 110, showed robust cell growth, and viability. The live/dead stain of the matrix at ABI showed that the culture was approaching near tissue density. Many more live cells were visible than dead cells. Even though many cells sloughed off during the staining procedure, cells were distributed throughout the woven fabric arrangement. Large aggregations of cells had uniformly attached at the fiber junctions of the woven structure. The strain of the bioreactor body after disassembly showed that cells had migrated up the well and onto the top surface of the bioreactor at both inlets and outlet ports. Cytospins showed healthy cell morphology. Again, colony assays showed a high proportion of granulocytes and a small proportion of macrophage colonies. At the terminal harvest, the cells were over 83% viable in the regular harvest and 92% viable from the bioreactor drain. Eight (8) million cells were recovered from the regular harvest. The bioreactor drain taken less than a half hour later yielded an additional 16 million cells, for a total recovery of over 24 million cells.

The flow profile at the terminal harvest showed that almost all of the CD3+(Thymocytes, T cells) had disappeared while the CD19+ (B cells) cells had increased 10 fold from the original seeding (11% to 81%). CD 81+ cells (lymphocytes, B-cell co-receptor) went up over 30%. Additionally, there was a slight increase in thy 1+ stromal cells and CD41+ cells (platelets, megakaryocytes). The cytospins, along with the rapid rate of proliferation, was suspected to be due to a possible presence Epstein Barr transformed lymphomas in the culture. This was later discounted by analysis for the EBV virus.

A secondary culture in a newly prepared bioreactor was initiated from some of the cells recovered from the terminal harvest of this run. See Example 5 below.

Cells from the terminal harvest from this experiment were used to seed a secondary culture in a 3-D bioreactor. The purpose of this "follow-on" experiment was to assess the potential of the cells harvested from a long-term bone marrow equivalent culture to function as a constant source of bone marrow cells to be used in further experimentation without the need to re-aspirate the human donor.

Example 4

Experiment Setup:

This run was designed to examine the reconstitution ability of the sloughed cells obtained from regular harvests of the bioreactors in the modified recirculating flow loops. This run contained one bioreactor containing three 19 mm diameter, one mm thick polypropylene matrices that were seeded with cells obtained from a bioreactor that had been cultured for 108 days. One hour prior to seeding with the previous experiment's cells, the bioreactor was inoculated with 3.5 million MSC'S. After allowing the MSC's to settle for one hour, 14 million cells from the bioreactor drain of the 108 day culture were seeded into the system. This system contained both an oxygen sensor in the upper gas chamber as well as a dissolved oxygen probe that was incorporated inline with the flow loop.

Procedure:

Flow loops were sterilized and conditioned with complete LTBMC media for one hour. The system was inoculated as described in the experimental setup. Two million cells were given to flow cytometry for an analysis of the inoculums.

Circulation was started 48 hours post seeding.

Beginning on day 4 three mL of media containing cells was harvested daily from the bioreactor on Tuesdays, Thursdays, and Saturdays for the duration of the experiment. Cell and viability counts, lactate analysis, Flow cytometry, colony assays, cytospins, and discounts were regularly preformed on the harvested cells.

On day 376, the experiment was terminated. 7.5 mL of media was drained from the bioreactor and 30 mL was collected from the buffer and tubing. Cells were counted manually and lactate analysis was conducted. Photographs were taken of the system before harvest and after the bioreactor was disassembled. One million cells were given to flow cytometry for analysis. Cytospins and colony assays were done on the remaining cells. The supernatants were frozen for cytokine analysis. Cells were also frozen for future analysis. All matrices were removed and placed in pre-warmed DPBS. A small section was images with SEM. The other matrices were fixed with 2% Gluteraldehyde. Tissue formation was photographed under bright field Microscopy. Digital photographs were taken of the matrices, snap rings, as well as the bioreactor.

Results and Discussion.

Figure 4A:
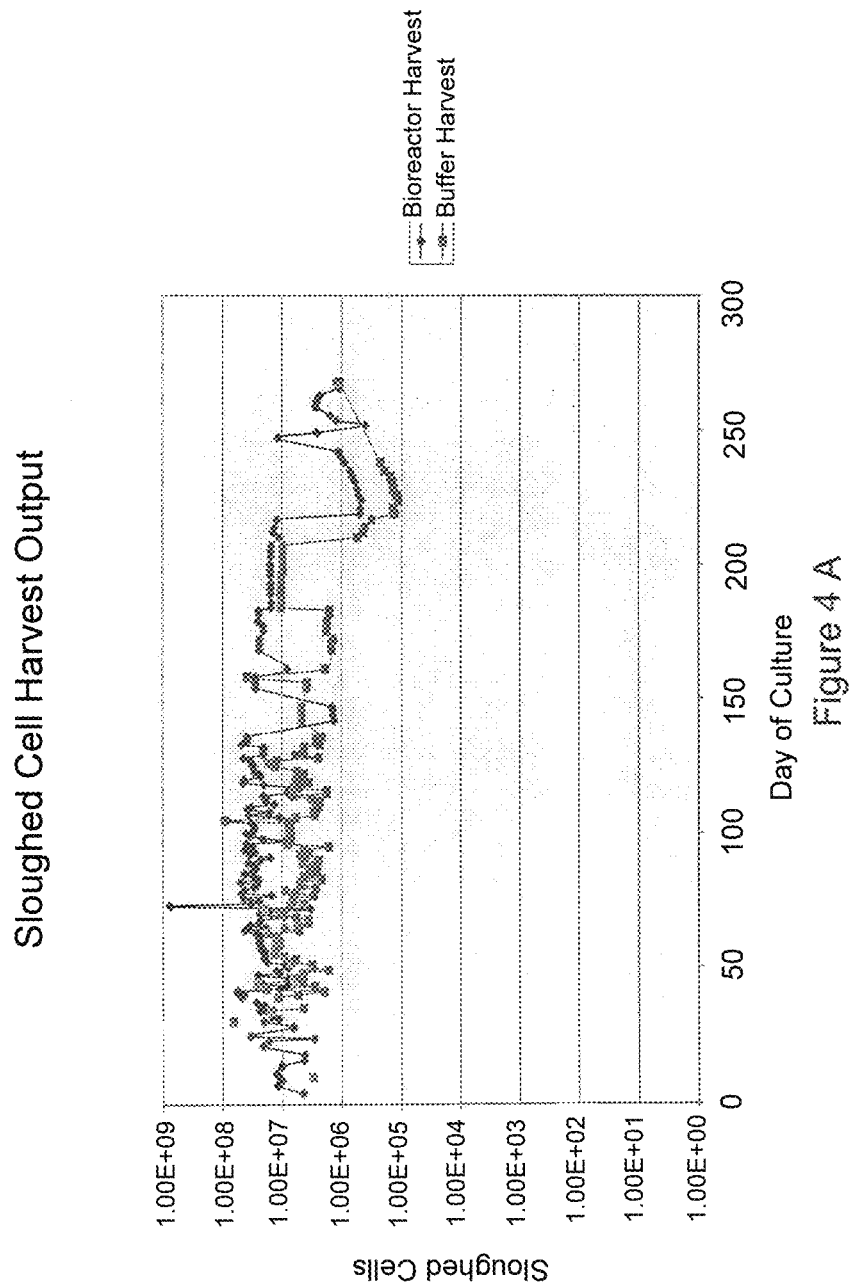
Figure 4B:
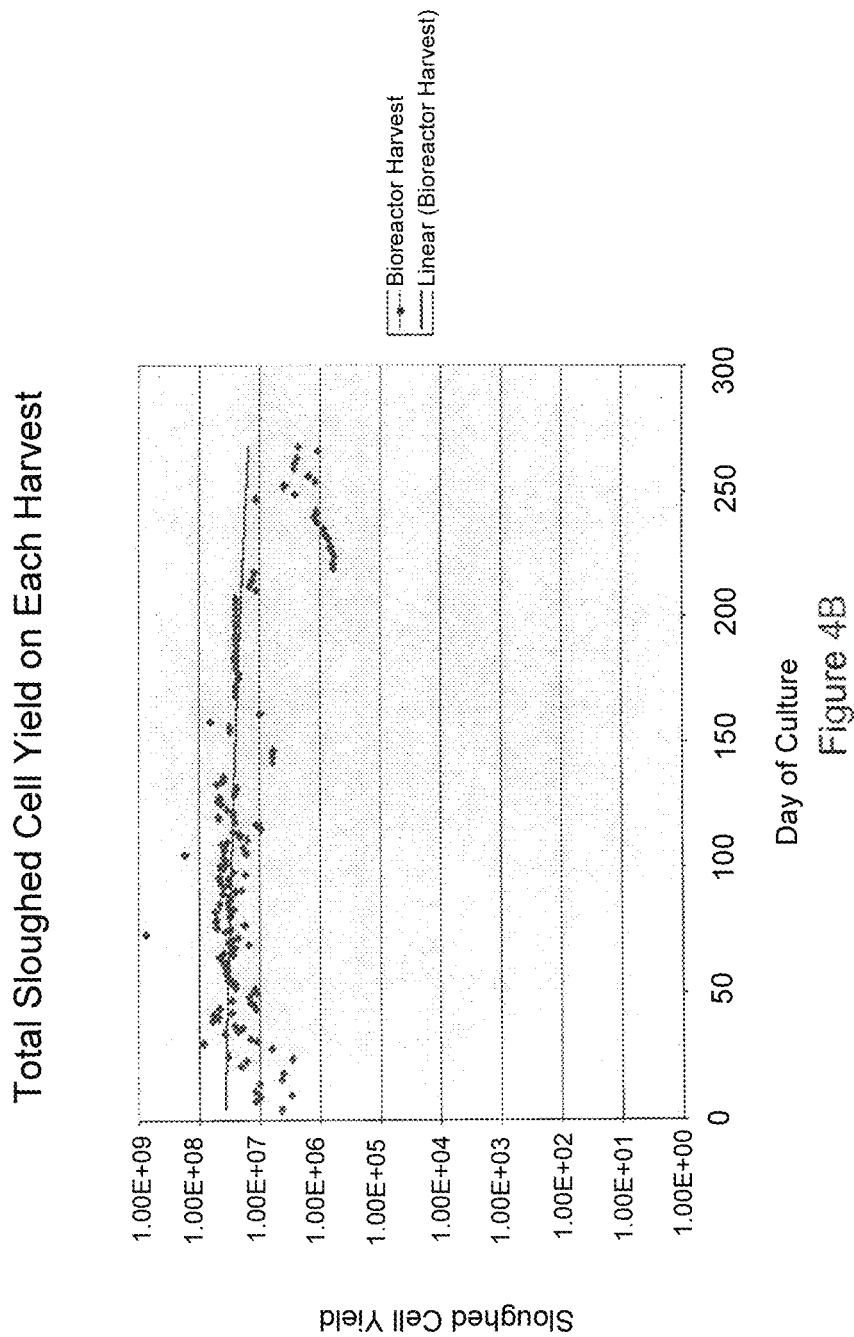
Figure 4:
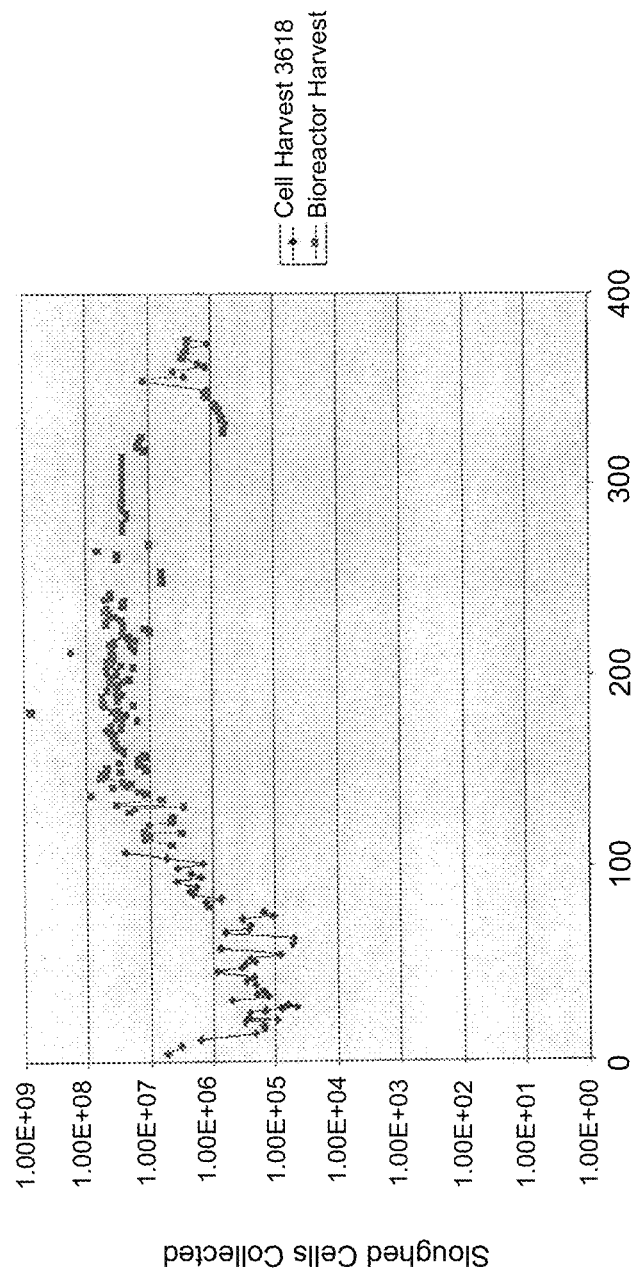

Cell counts can be seen in the graphs depicted in FIGS. 4A, B and C. Cell output remains high throughout the experiment, however viability fluctuates significantly. Buffer yields tend to be lower than bioreactor outputs. The graph in FIG. 4B illustrates the combined cell yields of the bioreactor and the buffer per harvest. Cell yields typically remain over one million cells. The graph in FIG. 4C depicts the average yield per day for every ten days post inoculation.

The sloughed cells analyzed for in flow cytometry parallel the results seen for peripheral blood for CD34, CD14, and CD45+ circulation. The following chart shows flow marker percentages for selected time points during this experiment. This data shows elevated percentages of markers seen on a variety of activated cells (CD45+, 19, 41). CD34, 90, 16, 3 are seen in small percentages throughout the experiment, suggesting that early cells are also being released. Assay results show IL-8, MIP-1b, 1P-10, IL-4, and IFN-g are also being detected in the media. These markers are involved in cell maintenance, adhesion, regulation and activation of a variety of cell types. CFU-GM assays also reveal differentiate cells capable of reconstituting themselves.

Figure 5:
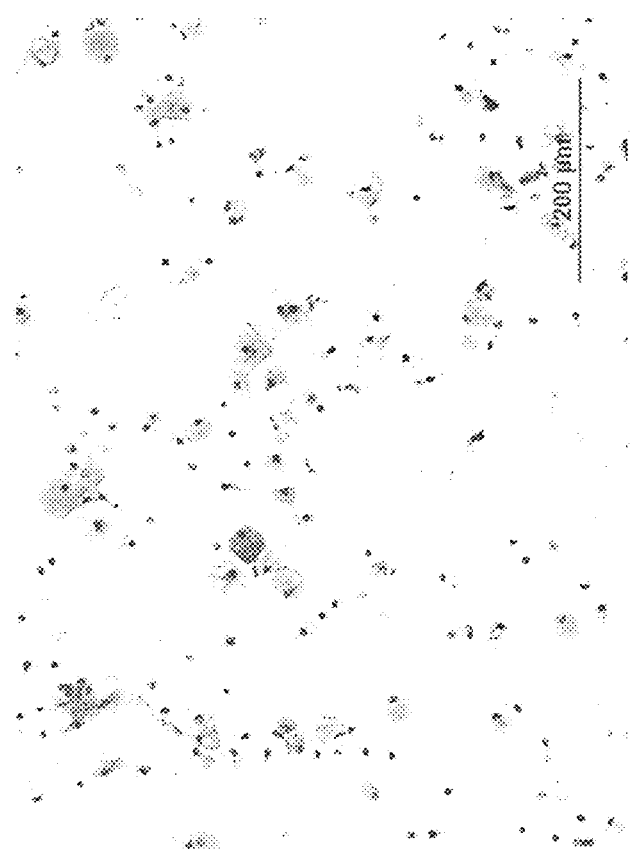
FIG. 5 shows a cytospin depicting a normal bone marrow morphology obtained from the culture stained with Giemsa orange stain.

FIG. 5 shows that cytospins obtained from the culture stained with Giemsa orange stain reveal a diverse morphology of releasing cells at 376 days.

Figure 6:
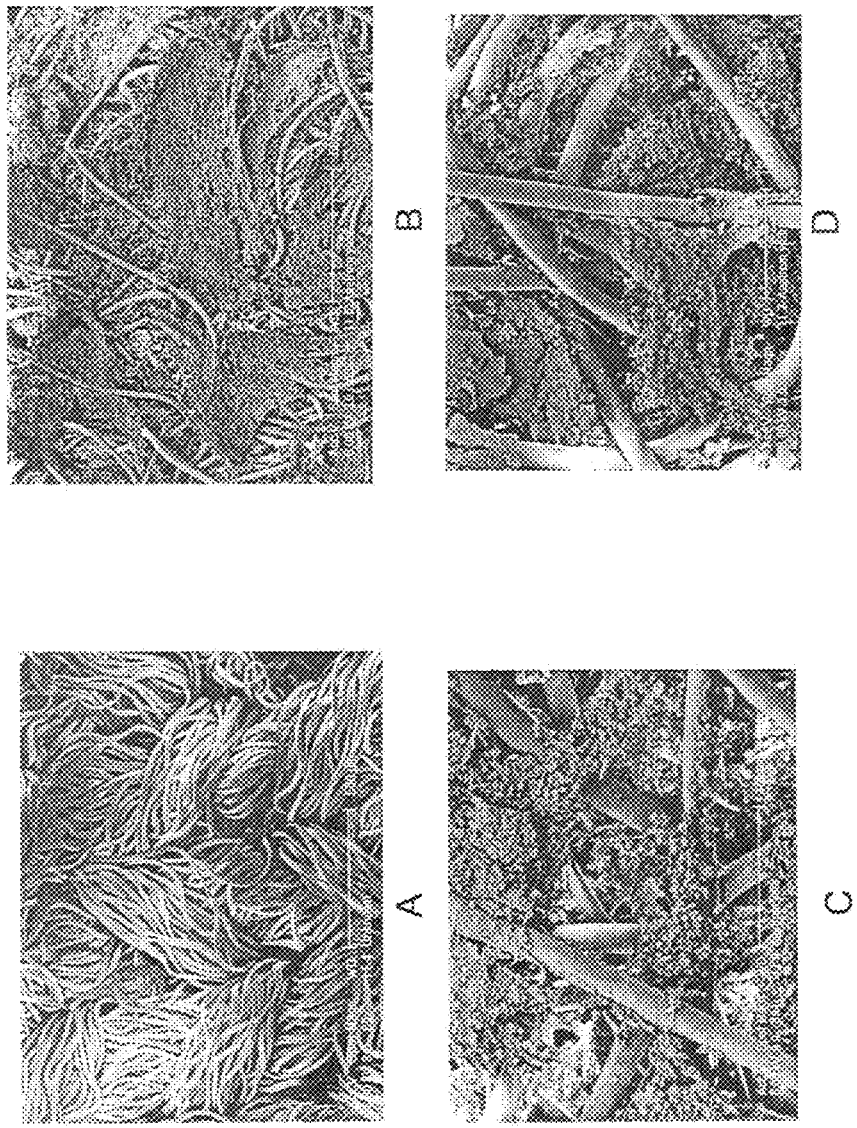
FIG. 6 A-V depicts various images of scanning electron microscopy (SEM) at day 376, day 268 post re-seeding with FIG. 6A showing a SEM micrograph of a blank matrix.

FIG. 6 depicts various images of scanning electron microscopy at day 376, day 268 post re-seeding. FIG. 6A depicts a blank matrix and FIGS. 6B-V show extensive cell growth, on and within the matrix. These images demonstrate that the bone marrow cells prefer to arrange themselves in close associations with cells of varying morphology and size typical of normal bone marrow.

The bioreactor was also visually inspected upon termination of the experiment and tissue can be seen on the snap rings and the bioreactor body.

Throughout the culture, this bioreactor produced an average of over one million cells in each daily harvest. Upon termination, tissue could be seen with the naked eye, spanning across the wells of our older version bioreactor. SEM photographs show that cells on the matrix appear to be at near tissue density ($10^9$ cells/cm$^2$). This is significant in culture that yielded a million cells daily and 2.5 million cells in the terminal drain of the bioreactor. Supernatants reveal cytokine release consistent with tissue maintenance and wide array of cells, supporting the diverse markers reported by flow cytometry.

An object of this invention was to provide an apparatus in which a mixed population of cells such that the cells were provided with an environment where they can reorganize into a tissue-like array, be maintained without sub-culture for extended periods of time, and have the capacity to support tissue function. This experiment fulfills this objective. The fact that the releasing cells from a previous experiment were able to repopulate the bioreactor, and still maintain tissue organization and releasing cells for an additions 250+ days can be considered an accomplishment. The flow data, colony, cytokine, and mouse experiments eliminate any question of functionality.

Obviously, numerous modifications and variations of the present invention are possible in light of the above teachings. It is therefore to be understood that within the scope of the appended claims, the invention may be practiced otherwise than as specifically described herein.

The invention claimed is:

1. A method of providing a therapeutic benefit to a patient, comprising generating, ex vivo, a matrix of cells that mimics at least one phenotype of a naturally occurring mammalian tissue, the method comprising introducing stem cells, progenitor cells, mature cells or a mixture of these into a bioreactor, the bioreactor comprising:
   (i) a matrix material configured to receive cells in a first fluid,
   (ii) a first chamber configured to flow the first fluid including the cells to the matrix material;
   (iii) a first gas permeable membrane configured to permit a first gas to flow therethrough to the first fluid in the first chamber; and
   (iv) a gassing chamber operably linked to the first chamber, said gassing chamber providing gas that flows through the first gas permeable membrane; providing a culture medium to the bioreactor for a time and under conditions suitable for the cells to arrange on the matrix material of the bioreactor whereby the cells so arranged mimic at least one phenotype of a naturally occurring mammalian tissue; and providing the ex vivo generated matrix of cells to the patient to provide a therapeutic benefit thereto.

2. A method of providing a therapeutic benefit to a patient, comprising generating, ex vivo, a matrix of cells that mimics at least one phenotype of a naturally occurring mammalian tissue, the method comprising introducing stem cells, progenitor cells, mature cells or a mixture of these into a bioreactor, the bioreactor comprising:
   (v) a matrix material configured to receive cells in a first fluid,
   (vi) a first chamber configured to flow the first fluid including the cells to the matrix material;
   (vii) a first gas permeable membrane configured to permit a first gas to flow therethrough to the first fluid in the first chamber; and
   (viii) a gassing chamber operably linked to the first chamber, said gassing chamber providing gas that flows through the first gas permeable membrane;

providing a culture medium to the bioreactor for a time and under conditions suitable for the cells to arrange on the matrix material of the bioreactor whereby the cells so arranged mimic at least one phenotype of a naturally occurring mammalian tissue;

harvesting the cells which are released into the culture medium; and providing the harvested cultured cells to the patient to provide a therapeutic benefit thereto.

* * * * *